US012607692B2

(12) United States Patent
Knopke et al.

(10) Patent No.: US 12,607,692 B2
(45) Date of Patent: Apr. 21, 2026

(54) IMPLANTABLE BIOSENSOR CONTAINING A MAGNETIC NANOPARTICLE ASSAY FOR IN VIVO ANALYTE DETECTION

(71) Applicant: Lodestone Biomedical Inc., Lebanon, NH (US)

(72) Inventors: Christian Knopke, Redmond, WA (US); Solomon G. Diamond, Hanover, NH (US)

(73) Assignee: Lodestone Biomedical Inc., Lebanon, NH (US)

( * ) Notice: Subject to any disclaimer, the term of this patent is extended or adjusted under 35 U.S.C. 154(b) by 88 days.

(21) Appl. No.: 18/705,936

(22) PCT Filed: Nov. 1, 2022

(86) PCT No.: PCT/US2022/079065
§ 371 (c)(1),
(2) Date: Apr. 29, 2024

(87) PCT Pub. No.: WO2023/081650
PCT Pub. Date: May 11, 2023

(65) Prior Publication Data
US 2024/0418807 A1     Dec. 19, 2024

Related U.S. Application Data

(60) Provisional application No. 63/274,801, filed on Nov. 2, 2021.

(51) Int. Cl.
*G01R 33/12*        (2006.01)
*B22F 1/054*        (2022.01)
(Continued)

(52) U.S. Cl.
CPC .......... *G01R 33/1269* (2013.01); *B22F 1/054* (2022.01); *B22F 1/07* (2022.01);
(Continued)

(58) Field of Classification Search
CPC .............................. G01R 33/1269; B22F 1/16
(Continued)

(56) References Cited

U.S. PATENT DOCUMENTS

2005/0271745 A1    12/2005 Gruettner et al.
2008/0071178 A1    3/2008 Greenland et al.
(Continued)

FOREIGN PATENT DOCUMENTS

EP        1889572        2/2008
WO      2013188765      12/2013

OTHER PUBLICATIONS

Preliminary Report on Patentability mailed May 16, 2024, Internationa Application No. PCT/US2022/079065, Internation Filing Date Nov. 1, 2022.
(Continued)

*Primary Examiner* — Roberto Velez
(74) *Attorney, Agent, or Firm* — Summit Patents PC

(57)                ABSTRACT

The system disclosed comprises an apparatus and a method for the detection and quantification of targeted molecules in vivo. The apparatus comprises an implantable biosensor and an AC magnetic detection device. The implantable biosensor includes functionalized nanoparticles functionalized with one or more moieties that bind to a molecular target of interest. The nanoparticles are retained in a biocompatible container which allows the molecular target of interest to enter the biosensor, for example through a semipermeable port. The biosensor can be implanted minimally-invasively into humans or animals. Upon exposure of the nanoparticles to the molecular target, a change in Neel relaxation time can be externally detected and correlated to the target analytes concentration. The change in relaxation time is detected through magnetic AC spectrometric measurements at a frequency specifically tuned to the nanoparticle type of (Continued)

interest Additionally, a method is provided for quantifying one or several biosensors within one specimen.

25 Claims, 12 Drawing Sheets

(51) Int. Cl.
| | |
|---|---|
| *B22F 1/07* | (2022.01) |
| *B22F 1/16* | (2022.01) |
| *B22F 1/17* | (2022.01) |
| *G01N 33/543* | (2006.01) |

(52) U.S. Cl.
CPC .................. *B22F 1/16* (2022.01); *B22F 1/17* (2022.01); *G01N 33/54326* (2013.01); *G01N 2446/80* (2013.01)

(58) Field of Classification Search
USPC ......................................................... 324/228
See application file for complete search history.

(56) References Cited

U.S. PATENT DOCUMENTS

| | | | |
|---|---|---|---|
| 2011/0105825 A1* | 5/2011 | Nayfach-Battilana | ...................... A61K 49/183 600/12 |
| 2020/0284787 A1* | 9/2020 | Cabrera Carrasco | ...................... G01N 33/553 |

OTHER PUBLICATIONS

Basini et al. Local spin dynamics of iron oxide magnetic nanoparticles dispersed in different solvents with variable size and shape: A 1 H NMR study, J Chem Phys, Jan. 18, 2017, vol. 146:034703, pp. 1-10. entire document.

International Search Report and Written Opinion mailed Feb. 2, 2023, International Application No. PCT/US2022/079065, International Filing Date Nov. 1, 2022.

* cited by examiner

*A*

*B*

*A*

*111*

*B*

*100*

*107*

*112*

*A*

*B*

*A*

*B*

■ *20 nm particles - sulfo NHS - Glycene*
▲ *20 nm particles - sulfo NHS - Ocean NanoTech QB*
◆ *25 nm Particles - sulfo NHS - Ocean NanoTech QB*
● *25 nm Particles - no sulfo NHS - Ocean NanoTech QB*

IMPLANTABLE BIOSENSOR CONTAINING A MAGNETIC NANOPARTICLE ASSAY FOR IN VIVO ANALYTE DETECTION

CROSS-REFERENCE TO RELATED APPLICATIONS

This application is a 371 filing of International Patent Application No. PCT/US22/79065, filed Nov. 1, 2022. "IMPLANTABLE BIOSENSOR CONTAINING A MAGNETIC NANOPARTICLE ASSAY FOR IN VIVO ANALYTE DETECTION." which claims priority and benefit from This application claim benefit from U.S. Provisional Application No. 63/274,801, entitled, "IMPLANTABLE BIOSENSOR CONTAINING A FUNCTIONALIZED NANOPARTICLE ASSAY FOR IN VIVO ANALYTE DETECTION," filed Nov. 2, 2021, which is incorporated herein by reference in its entirety for all purposes.

FIELD OF INVENTION

The present invention generally relates to an apparatus and a method for measuring biomolecules. In particular, the present invention relates to methods for quantitatively measuring biomolecules by using functionalized nanoparticles in vivo.

BACKGROUND

The detection and quantification of endogenous or pathogenic biomarkers is an important cornerstone of modern medicine. Treatment decisions are often based on the presence of specific biomarkers detected in blood or tissue samples. Colorimetric immunoassays with monoclonal antibodies and other in vitro tests are now part of every hospital laboratory. While in vitro blood tests reveal information about the whole body, they lack local information that is typically obtained with invasive tissue biopsies at a single time point.

For example, in checkpoint inhibitor therapy, specific regulatory molecules of the immune system are targeted to dampen or stimulate the host's immune response to cancer. One of those regulatory molecules expressed on immune cells is PD-1, which interacts with the surface protein PD-L1. The upregulation of PD-L1 on cancer cells seems to inhibit the ability of T-cells to fight the cancer cells. Current checkpoint inhibitor strategies target PD-1 or PD-L1 with respective antibodies. While these therapies are successful in a significant number of cases, the number of non-responders and patients with adverse events is still very high. Due to the complex nature of cell-signaling pathways the search for truly predictive biomarkers has been unsuccessful for many immune-therapies. In this example, PD-L1 protein expression on tumor or immune cells was quantified on biopsy samples and emerged as the first potential predictive biomarker for check-point inhibitor therapy. However, this biomarker was only predictive in roughly 30% of the cases (Davis, Andrew A., and Vaibhav G. Patel. "The role of PD-L1 expression as a predictive biomarker: an analysis of all US Food and Drug Administration (FDA) approvals of immune checkpoint inhibitors." Journal for immunotherapy of cancer 7.1 (2019): 1-8.).

With the lack of truly predictive biomarkers, clinicians often apply treatments based on statistical success rates, rather than individual suitability. They then evaluate the individual efficacy through response or surrogate markers.

The current state of the art in evaluating the efficacy of cancer treatments is measuring the tumor size (also called Tumor burden or Tumor load) via computer tomographic (CT) or magnetic resonance imaging (MRI) at different timepoints throughout the treatment. For some cancers, the concentration of circulating cancer cells in the blood is correlated with successful cancer treatment. These surrogate markers are important cornerstones of clinical trials.

However, unlike surrogate markers, directly related biomarkers such as progression free survival, are not always measurable within the timeframe of the trial.

For immuno-oncology, traditional clinical endpoints from chemo- and radiotherapy are not sufficient. Biomarker driven surrogate endpoints are needed to evaluate the progress of the therapy on a local level. (Anagnostou, Valsamo, et al. "Immuno-oncology trial endpoints: capturing clinically meaningful activity." (2017): 4959-4969.)

Information about the local concentration of regulatory molecules, their respective antibodies and sequential biomarkers that indicate the efficacy of the therapy are crucial information for the attending physician. Based on this information the physician can up- or downregulate, or even change the administration of the checkpoint inhibitor drug.

The state-of-the-art colorimetric in vitro assay technology does not address the challenges of in vivo measurements and is unsuitable for deep tissue measurements.

An alternative approach to obtain the needed deep tissue data can be found in functionalized contrast agents for full body imaging techniques, such as MRI or magnetic particle imaging (MPI). Functionalized magnetic contrast agents have been proposed and patented before. There are however major technical, regulatory, and economic barriers that prevent successful clinical translation. Technical questions about the half-life of the nanoparticles, biodistribution, potential for adverse events such as clotting or organ damage need to be addressed. The regulatory hurdles to getting a new MRI contrast agent approved by the Food and Drug Administration are large and time consuming. The economics of bringing a new contrast agent to market only make financial sense in a few cases. An in vivo platform technology for various molecular targets based on a functionalized contrast agent alone is therefore unlikely to see clinical applications.

DETAILED DESCRIPTION

Figure 1:
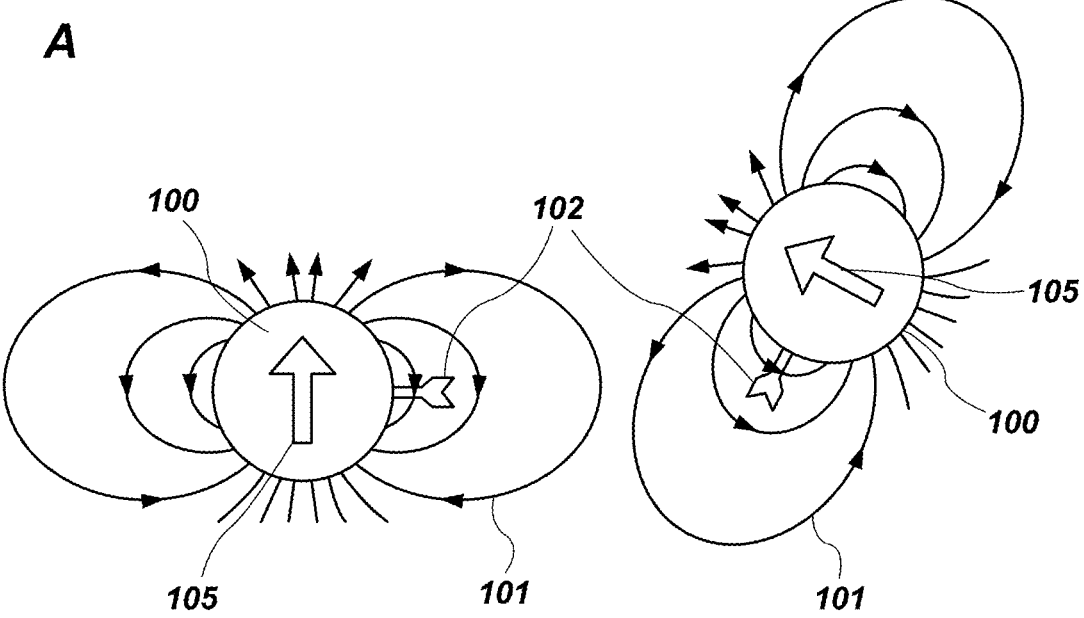
FIG. 1 illustrates functionalized nanoparticles in unaggregated (A) and aggregated state (B); upon exposure to the targeted molecule, the nanoparticles and targeted molecules aggregate.
Figure 1:
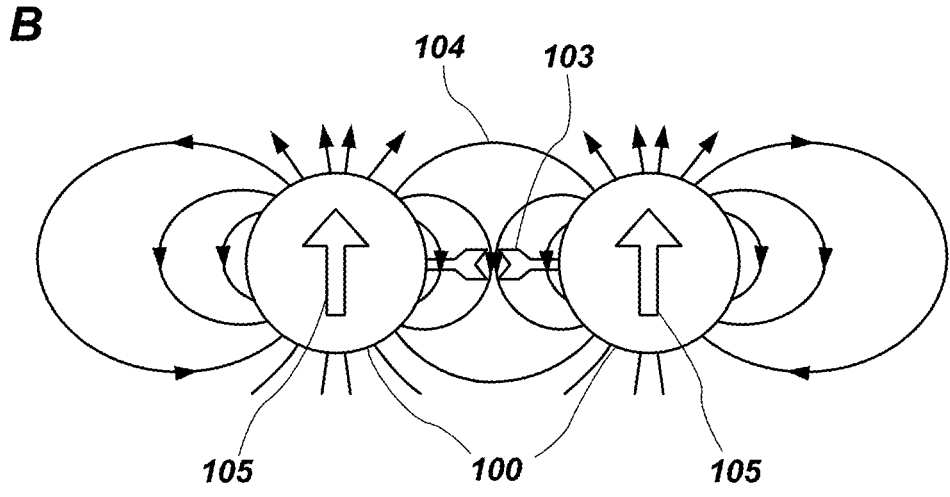

The here disclosed apparatus comprises an implantable biosensor and an alternating current (AC) magnetic measurement device, wherein the biosensor comprises functionalized nanoparticles and a biocompatible container.

The implantable biosensor is capable of interacting with specific targeted molecules within its vicinity. The biosensor contains functionalized nanoparticles whose magnetic response signal can be externally read out via AC spectroscopic means. The magnetic response signal is the detected magnetic field of the nanoparticles while they are exposed to an external AC drive field. The magnetic response signal can be analyzed for parameters such as the harmonic spectrum obtained by Fourier transformation, remanence, coercivity, maximal magnetization, or hysteresis loop.

The signal from the biosensor corresponds to the local concentration of the targeted molecules in the draft area of the sensor at the time of measurement. In another implementation the signal of the sensor corresponds to the accumulated exposure of the biosensor to the targeted molecules. Knowing the concentrations of targeted biomarkers in specific locations in the body has clinical value, as it helps the clinician to make more informed treatment decisions in different cancer therapies, such as immunotherapy.

The nanoparticles retained in the biocompatible container are functionalized with one or several specific binding agents. The interaction with the targeted biomolecules changes the aggregation state of the functionalized nanoparticles within the implantable biosensor. The change in aggregation of the nanoparticles in combination with the targeted biomolecules results in an increase or decrease of dipolar interaction between the nanoparticles. The dipolar interaction changes the Neel relaxation time of the nanoparticle-biomolecule aggregates which can be externally measured via low field AC spectroscopic means. The biosensor can be designed in a way, so that the nanoparticles form aggregates with the target when they come into contact with the targeted biomolecule. In an alternative implementation the nanoparticles are initially in an aggregated cluster which disassociates when exposed to the targeted biomolecule.

The biosensor may target a wide range of molecules including nucleic acid strands, proteins, sugars, biologics, biosimilars, or metabolites. In another embodiment, the sensor may be designed in a way that aggregation only occurs when a combination of a targeted drug and endogenous molecule are present and interacting. In this embodiment, the sensor confirms that the drug reached the area of interest and interacted with its designated target.

In another embodiment, the biosensor contains different types of functionalized nanoparticles that target different molecules. In one instance iron oxide nanoparticles are doped with different ions such as yttrium, magnesium, zinc, or copper which changes their AC magnetic response. In another instance the iron oxide nanoparticles have core sizes, such as 15 nm, 20 nm or 25 nm, which can also be used to distinguish the nanoparticles based on their magnetic response. In yet another instance the nanoparticles are either rod shaped, cubical or spherical, which in turn affects their magnetic response and can be used to differentiate them. In another instance the nanoparticles are differentiated through a combination of magnetic core parameters like shape, size, composition, or a combination thereof.

In another embodiment, a biocompatible container for at least one type of functionalized nanoparticle is provided. In one implementation, the container retains the nanoparticles with a permeable or semipermeable membrane while at the same time allowing the intra- or extracellular fluid to interact with the nanoparticles. The biocompatible container is designed for minimally-invasive implantation in humans or animals and can be biodegradable.

In another embodiment, the container is a biocompatible matrix comprising a polymer or polysaccharide. The matrix retains the functionalized nanoparticles while at the same time allowing the intra- or extracellular fluid to interact with the nanoparticles and the nanoparticles to bind to each other by sharing a targeted molecule. The matrix is designed for minimally-invasive implantation in humans or animals and can be biodegradable.

In yet another embodiment, a biocompatible container for at least one type of functionalized nanoparticle is provided. The enclosure retains the nanoparticles while at the same time allowing the intracellular, extracellular, or interstitial fluid to interact with the nanoparticles. The functionalized nanoparticles are immobilized on the surface of a larger non-magnetic body such as a non-magnetic bead. The nanoparticles are still able to bind to each other by sharing a targeted molecule. The container is designed for minimally-invasive implantation in humans or animals and can be biodegradable.

The disclosed apparatus includes an AC magnetic measurement device. The device consists of two main groups, magnetization elements and detection elements. The magnetization elements generate AC magnetic fields in the range of 100 Hz to 20 kHz and a field strength of up to 20 mT. The magnetization elements are arranged in a way that allows deep tissue penetration of the magnetic field. In one implementation the magnetization element comprises a tubular form, magnetizing a sample space within a tube. In another implementation the magnetization element comprises an open form, magnetizing a sample space adjacent to the elements. In yet another implementation the magnetization elements comprise a semi-closed C-shape or horseshoe form, magnetizing the sample space enclosed by the magnetization elements. In this implementation the detection elements comprise thermally stabilized gradiometer coils. In other implementations the detection elements comprise superconducting quantum interference device (SQUID) sensors, giant magnetoresistance (GMR) sensors, or optical magnetometers. In this embodiment the magnetic measurement comprises the harmonic spectrum obtained by Fourier transformation of the detected AC signal. In other implementations of the disclosed apparatus the AC measurement obtains measurable parameters such as remanence, coercivity, maximal magnetization, or hysteresis loop parameters.

The here disclosed system includes a method for measuring a biosensor in human or animal. The method includes the exposure of the implanted biosensor to external AC magnetic fields and detecting the strongest magnetic response through several scans. The method also includes positioning the magnetization and detection unit above the implanted biosensor and the detection of the AC magnetic response signal of the nanoparticles enclosed in the biocompatible container. Furthermore, the method includes calculating the concentration of the analyte from a calibration curve of AC magnetic responses from known concentrations of the analyte interacting with the nanoparticles.

The method further includes the analysis of the magnetic Neel relaxation time by AC spectroscopic means and the correlation of the response signal to the concentration of the targeted molecule or molecules. The method further includes the utilization of AC magnetic fields and frequencies that are below the nerve stimulation threshold for humans.

In another embodiment, a minimally-invasive implantable biosensor is provided that contains at least one type of nanoparticle functionalized with binding sites for a cytokine, a drug, RNA, DNA, a protein, a peptide, a sugar, a fat, a biosimilar, an antibody, an antibody fragment, or a combination thereof. The AC magnetic response signal of the nanoparticles correlates to the local concentration of the bound molecule within the biosensor. Depending on the nanoparticle functionalization type the change in magnetic signal corresponds either to the concentration at time of measurement or the accumulated exposure since implantation of the sensor.

Additionally, a method is provided to analyze several targeted molecules with one biosensor. The biocompatible container holds several types of functionalized nanoparticles that are each functionalized for different targeted molecules. The nanoparticles can be differentiated through their magnetic response to the externally applied AC magnetic field. The magnetic response depends on the size, shape, and composition of their respective magnetic cores. The ability to differentiate several magnetic responses within a single biocompatible container enables multiplexing of several targeted molecules. In yet another embodiment, the aggregates of a specific analyte are combinations of nanoparticles with different shapes, sizes, or composition.

The here disclosed system includes a method for detecting two or more implanted biosensors in a single subject in vivo. The method includes distinguishing the implanted biosensors based on their AC magnetic response and local field strength. In one instance the method includes the use of non-linear least square fitting, such as the Levenberg-Marquardt algorithm, to determine the position and magnetic moment of the implanted biosensors using models and assumptions. In one instance the model is a multiple magnetic dipole model with a known number of dipoles equaling the number of implanted biosensors. In another instance the magnetic field of the implanted biosensors is assumed to be a magnetic dipole. In another instance the implanted biosensors are exposed to different magnetic fields and/or frequencies to enable their differentiation. In one implementation at least one implanted biosensor is driven into magnetic saturation during the measurement. In another implementation the implanted biosensors are exposed to a linear gradient field. In yet another implementation the implanted biosensors are exposed to different fields through the use of additional surface coils. Detection of several implanted biosensors at the same time enables the operator to obtain more medically relevant in vivo information. In one instance this information includes the quantification of the targeted molecule at the region of interest and a control site. This enables the operator to correlate the concentration of a targeted molecule in relative terms between the two measurement regions, providing a more complete picture of the biodistribution of the targeted molecule. In another embodiment this information includes the quantification of a secondary target in the region of interest or at a control site.

In one embodiment, a method is provided for detecting targeted biomolecules of interest in the tumor microenvironment. The method includes exposing at least one type of functionalized nanoparticle to extracellular fluid from the tumor microenvironment; and measuring the change in Neel relaxation time of the biosensor with the help of external AC magnetic fields. The magnetic response is further correlated to the local concentration of the targeted molecule at the time of measurement or the accumulated concentration of the targeted molecule over time.

In yet another embodiment, a method is provided for the early detection of the tumor tissue response to cancer treatment such as immunotherapy treatment. The method includes implanting the biosensor in the tumor microenvironment before treatment begins. The method further includes the longitudinal measurement of the biosensor's magnetic response and the determination of the local concentration of a cytokine, a drug, RNA, DNA, a protein, a peptide, a sugar, a fat, a biosimilar, an antibody, an antibody fragment, or a combination thereof. Depending on the nanoparticle functionalization type, the change in magnetic signal corresponds to either the concentration at the time of measurement or the accumulated exposure since implantation of the biosensor.

Conventional Systems & Methods

Existing systems and methods can be grouped in two main categories: analyte-detecting functionalized nanoparticles that are directly injected in the bloodstream, referred to hereinafter as functionalized magnetic contrast agents, and analyte-detecting functionalized nanoparticles that are encapsulated before implantation, referred to hereinafter as nanoparticle-based biosensors. The disclosed system fits in the latter category and has elements that can also be found in the first category.

There are only few nanoparticle-based biosensors known in the art. While these biosensors avoided several of the challenges that functionalized magnetic contrast agents face, they did not address or only partly solved other issues that are specific for nanoparticle-biosensors: Biodegradability or fate of the sensor after implantation; Confounding effects of media viscosity on the nanoparticle signal or targeted interaction; Confounding effects of media pH value on the nanoparticle signal or targeted interaction; Confounding effects of media ion concentration on the nanoparticle signal or targeted interaction; Confounding effects of the biocompatible container and target diffusion on the nanoparticle assay; Economic viability/affordability; Non-specific binding of nanoparticles with colloids;

Biosensors known in the art describe an implantable container with semipermeable membrane, containing functionalized nanoparticles that bind to target molecules. However, these biosensors are based on analyzing the spin relaxation property of the implantable sensor, specifically the alteration of the transverse relaxivity (T2) of surrounding water protons. The here disclosed apparatus distinguishes itself from the conventional systems and methods through the type of nanoparticle used, the measurement device and the measured contrast mechanism.

Unlike biosensors that are based on the spin relaxation of hydrogen atoms the here disclosed system uses the direct detection of nanoparticles with characteristics optimized for AC magnetic readouts at low fields and frequencies. Furthermore, the signal contrast created by the here disclosed nanoparticles is independent of the viscosity of the surrounding media. In another embodiment, the measurement device disclosed here is optimized for the low field and frequency readout of the here described nanoparticle implants. This provides an economical advantage compared to the expensive imaging MRI technology employed by existing biosensors.

Other known biosensor types known in the field utilize an aggregation-based magnetic assay encapsulated in a porous container. These biosensors measure the Brownian relaxation of the nanoparticle and correlate the aggregation of the nanoparticles with the presence of an analyte. The here disclosed system measures nanoparticles whose magnetic relaxation is dominated by viscosity-independent Neel relaxation instead of Brownian relaxation. Measurements of Brownian relaxation on the other hand is especially susceptible to changes in viscosity.

Depending on the type and location, the viscosity of the fluid can vary between 0.8-1 cP for intracellular fluid (Luby-Phelps, Katherine. International review of cytology. Vol. 192. Academic Press, 1999. 189-221.) and 3.5 cP for interstitial fluid (Wei Yao, International journal of biological sciences 9.10 (2013): 1050.). Due to its uncontrolled cell growth, altered cell metabolism and bad vasculature, the viscosity of the tumor microenvironment can be severely different from healthy tissue. The effects of viscosity and other associated factors like oncotic pressure on nanomedicine have been described by Yadollah Omidi, and Jalch Barar in BioImpacts: BI 4.2 (2014): 55.

The disclosed biosensor is based on the Neel relaxation behavior of functionalized nanoparticles as opposed to Brownian relaxation behavior or the T2 relaxation of water protons. Neel relaxation is independent of the viscosity of the surrounding media and does not require the functionalized nanoparticle to be free floating. The here presented nanoparticles must fulfill specific requirements concerning their coating, charge, and nanoparticle size in order to be usable as a Neel-based aggregation assay. These requirements allow the nanoparticles to be susceptible to dipolar interaction in an aggregated state.

The second category of conventional systems and methods relates to functionalized magnetic contrast agents. The inventions in this group generally ignore or partially ignore the challenges associated with functionalized magnetic contrast agents. These challenges are: Effects of media viscosity on the particle nanoparticle signal or targeted interaction; Effects of media pH value on the nanoparticle signal or targeted interaction; Effects of media ion concentration on the nanoparticle signal or targeted interaction; Short half-life of injected nanoparticles; Uptake of nanoparticles by macrophages and other cells; Non-specific binding of nanoparticles with colloids or cell walls; Soft protein corona around nanoparticles limiting their targeted interaction; Particle diffusion out of the region of interest; Contrast to noise ratio unfavorable: large volumes of unaggregated nanoparticles outside of the region of interest interfere with measurement of physiological levels of analyte; Large volumes of nanoparticles are needed, which increases the likelihood of adverse reactions; Possibility of blood clots caused by nanoparticles in blood stream; Possible staining at the injection site; Human safe AC magnetic measurements; Economic viability/affordability;

One group of functionalized magnetic contrast agents measures the disaggregation of nanoparticle clusters in vivo. The nanoparticle clusters are held together by cleavable nonmagnetic sugars or proteins. Although these nanoparticle clusters are designed for an in vivo application, the nonspecific interaction with media colloids, biodistribution of the nanoparticles, or effects of pH value and viscosity of the surrounding media is often not addressed. This group of functionalized contrast agents envisions the detection of enzymes only, whereas the here disclosed system describes the detection of cytokines, hormones, soluble antibodies and other cell signaling small molecules.

Another group of in vivo analyte detection with functionalized contrast agents measures the magnetic signal of the nanoparticles in two steps then outputs the measured value. They envision a device where the magnetization step and the readout of the functionalized nanoparticle signal are events that are separated in time or place to avoid interference. In the disclosed system, the magnetization step and the detection step happen simultaneously and the magnetization signal is filtered out either through a post processing step on a computer or by electrical design, for example through a gradiometer coil setup.

Other groups of analyte detection assays with functionalized contrast agents utilize the advantages of measuring Neel relaxation with AC magnetic methods. However, they do not address the issues of unspecific binding with media colloids and thus require an additional washing or preprocessing step. This limits these methods to in vitro assays.

Other publications in the field of in vitro measurements are acknowledged below. They exhibit elements of the here disclosed system without addressing the challenges of translating these measurement procedures to an in vivo application.

Simulations and experimental data provided by Kai Wu et al. in Journal of Physics D: Applied Physics 52.33 (2019): 335002 show that significant dipolar interaction for commercially available nanoparticles (magnetic core size 30 nm) can be achieved by reducing the inter-particle distance below 120 nm.

The adverse effect of a thick coating on the dipolar interaction between functionalized nanoparticles has been investigated by Peter J. Santos, et al. and published in Journal of the American Chemical Society (2020) in their paper "Reinforcing Supramolecular Bonding with Magnetic Dipole Interactions to Assemble Dynamic Nanoparticle Superlattices".

The interdependence of nanoparticle size, measurement frequency, and effective relaxation time has been studied and published before by Ferguson, R. Matthew, et al. IEEE transactions on magnetics 49.7 (2013): 3441-3444.

The possibility to use the functionalized nanoparticles of different (hydrodynamic) sizes for multiplexing has been demonstrated Kyoungchul Park, et al. in Nanotechnology 22.8 (2011): 085501 for a sensor based on Brownian relaxation. A multiplexing method for a Neel-based sensor is with different magnetic core sizes is presented here.

Biosensor Description

The disclosed implantable biosensor comprises a biocompatible container and functionalized magnetic nanoparticles.

The function of the biosensor is to indicate the concentration of a targeted molecule in the draft area of the sensor, which is the region of tissue undergoing fluid exchange with the biosensor.

The targeted molecule may be a soluble substance that is produced by the host organism endogenously or an exogenous substance administered to the host organism and soluble in the implantation site of the sensor. For example, the target molecule may be a cell signaling cytokine that indicates activity of the host's immune system. In another example, the target molecule might be an intravenously injected drug and the sensor indicates the local drug concentration at the implantation site. The targeted molecule may be any of the following substances: a cytokine, a drug, RNA, DNA, a protein, a peptide, a sugar, a fat, a biosimilar, an antibody, an antibody fragment, or a combination thereof.

In an exemplary embodiment, the sensor may detect the local concentration of a cytokine such as interferon gamma, transforming growth factor beta, interleukin 2, interleukin 6, VEGF or a combination thereof.

The main function of the functionalized nanoparticles is the indication of targeted molecules through changes in their aggregation state. The nanoparticle design stands out from other nanoparticles known in the art through: a Neel-based magnetic contrast mechanism, which is ideal for viscosity-independent measurements; a non-magnetic coating, which reduces non-specific binding and protein corona; optimization of the nanoparticles' surface charge for stability in different pH and ion concentrations; a magnetic AC response which is optimized for human save low field AC measurements; size, shape, and composition, which is optimized for multiplexing. Through their design the nanoparticles over-come several of the challenges other in vivo detection methods face: Effects of media viscosity on the nanoparticle signal or targeted interaction; Effects of media pH value on the nanoparticle signal or targeted interaction; Effects of media ion concentration on the nanoparticle signal or targeted interaction; Non-specific binding of nanoparticles with colloids.

Furthermore, the assay design supports absolute measurements of target molecule concentrations. Existing in vitro assays often use amplification steps that make the measurement time dependent and relative. This often requires a calibration curve that has to be measured in parallel with the sample. The disclosed assay allows for the measured values to be output, then interpreted with prerecorded calibration curves.

The nanoparticles consist of a magnetic core and are stabilized with a nonmagnetic surface coating. In one exemplary embodiment the magnetic core comprises of iron oxide and the coating is comprised of dextran. The nanoparticles are of a size so that their magnetic relaxation time is dominated by Neel relaxation at the measurement frequency when measured at body temperature. The thickness of the non-magnetic coating layer is designed in a way that it allows dipolar interaction between individual nanoparticles. The nanoparticles may be functionalized. The term "binding" encompasses covalent bonds, ionic bonds, and other intermolecular or intramolecular interactions. In one exemplary embodiment the binding sites are antibodies. Methods for functionalizing nanoparticles are known in the art. The functionalization of the nanoparticles is performed in a way that allows at least two nanoparticles to share one binding partner. The sharing of one binding partner by at least two nanoparticles is further referred to as "aggregation." The nanoparticles are designed in a way that dipolar interaction between individual nanoparticles occurs in the event of aggregation. This is achieved by coating the magnetic core with a particularly thin coating relative to its core diameter. Additionally, the nanoparticle is functionalized in a way that the surface charge allows for a stable suspension in unbound state and dipole-dipole interaction in aggregated state. In one implementation a 2 nm thick dextran coating is applied to a 20 nm iron oxide core with a dopamine anchoring group. Alternatively, a thin dextran coating can be achieved by coating the nanoparticle core with PEG (molecular weight 2000) and then adding another layer of dextran. The nanoparticles are further designed in a way that the dipolar interaction is strong enough to cause a detectable change in the nanoparticle's Neel relaxation time.

FIG. 1A illustrates the individual functionalized nanoparticles 100 in their not aggregated state. In the illustration the magnetic dipole field of the magnetized nanoparticle is displayed as magnetic field-lines 101. The orientation of the magnetic moment 105 of the nanoparticle is illustrated as an arrow. Because the nanoparticles are not aggregated their magnetic dipole fields are not interacting. The Neel relaxation process, the internal re-orientation of the magnetic moment without rotation of the nanoparticle, is not affected by dipolar interaction. The individual nanoparticles express binding sites 102 on their surface.

In FIG. 1 B the nanoparticles are displayed in an aggregated state where they crosslink through the shared binding on a target of interest 103. Due to the proximity of the nanoparticles the dipole fields are now interacting 104 and the individual Neel relaxation time is altered. Their magnetic moments 105 can no longer relax independently.

The term "local concentration" refers to the concentration of targeted molecule in the draft area of the sensor. The draft area of the biosensor is the region of fluid exchange between the biosensor and the surrounding tissue, the geometry of the container retaining the nanoparticles and the characteristics of the container's opening, for example a semipermeable membrane. In an exemplary implementation, the biosensor is cylindrical with a length of 10 mm and an outer diameter of 0.75 mm, resulting in a draft area of approximately 1 cubic centimeter. The term "at the time of measurement" includes the time needed for the concentration within the sensor to equalize with the concentration in the draft area and the time for a target molecule to interact with the functionalized nanoparticles. The term "accumulated exposure" refers to all interactions the sensor had with the target molecule from the time of implantation to the time of measurement.

In an exemplary embodiment, the biosensor is minimal-invasively implantable with an 18-gauge needle that is otherwise used for tissue biopsies. The biosensor may be injectable and implantable within a patient. The term "injectable" refers to the method of implantation. In this case, the sensor might be placed with a needle and stylet. The sensor may be deployed in the body for a definite period of time to perform measurements during this time. In another implementation, the sensor may be made of a biodegradable material with a defined breakdown time.

In yet another implementation, the sensor might be attached to a tether which runs along the injection channel. During the measurement period the tether is covered by an adhesive bandage or band-aid. The tether can be used to safely remove the sensor at the end of the measurement period.

In an embodiment, the biosensor is designed small enough to be injectable with a syringe or placed with a biopsy needle and stylet. In one embodiment, the biosensor may be implanted minimally invasively in the tumor microenvironment. The term "minimally invasively" refers to a method of placement which is less invasive than an open surgery, such as placement with a needle, catheter, or endoscopically. Minimally invasive biosensor placement may use image guidance with ultrasound or x-ray.

The biocompatible container's main function is to retain the nanoparticles while allowing the targeted molecule to interact with the nanoparticles. Through the retention of the nanoparticles in the region of interest, the apparatus overcomes several challenges that functionalized contrast agents face. These advantages include: Long half-life of injected nanoparticles; No uptake of nanoparticles by macrophages and other cells; Less non-specific binding of nanoparticles with colloids; No non-specific binding of nanoparticles with cell walls; Reduced soft protein corona around nanoparticles limiting their targeted interaction; No nanoparticle diffusion out of the region of interest; Favorable contrast to noise ratio: small volumes of unaggregated nanoparticles compared to aggregated nanoparticles at physiological levels of target molecules; Very small volumes of nanoparticles are needed, which minimizes the likelihood of adverse reactions; No blood cloths caused by nanoparticles in blood stream; No staining at the injection site by remaining subcutaneous nanoparticles.

There are several embodiments disclosed herein on how the container can achieve this. Additionally, materials are disclosed which give the container the ability to be biocompatible or even biodegradable.

In one exemplary embodiment, the minimally invasive biosensor may consist of a container made of a semipermeable membrane. The semipermeable membrane has a pore size big enough to allow small molecules such as cytokines to enter the sensor, but small enough to keep nanoparticles in the sensor. In one implementation the membrane has a molecular weight cutoff of 750 kDa and the nanoparticle has a core diameter of 25 nm. The nanoparticles within the sensor are functionalized to bind to at least one targeted molecule. The nanoparticles may be superparamagnetic and may be comprised of an iron oxide core. Depending on the type of functionalization the binding mechanism of the nanoparticle to the target may be strong or weak. If the nanoparticle is functionalized with a strong binding mechanism the target of interest will stay connected to the nanoparticle, even if the concentration in the draft area later decreases. A sensor with a strong binding mechanism will accumulate the targeted molecule over time and its magnetic signal change will reflect the integrated amount of targeted molecule in the draft area. This type of sensor will be further referred to as an "integrating sensor." A sensor with a weak binding mechanism will lose its binding partner if the concentration in the draft area decreases after the binding event. Its magnetic signal change will reflect the local concentration of the targeted molecule in the draft area at the time of measurement. This type of sensor will be further referred to as "contemporary sensor." In an exemplary embodiment, the nanoparticles may be functionalized with an antibody a cytokine, a drug, RNA, DNA, a protein, a peptide, a sugar, a fat, a biosimilar, an antibody, an antibody fragment, a molecularly imprinted polymer (MIP), or a combination thereof.

FIG. 2A illustrates functionalized nanoparticles encased in a semipermeable membrane 106. The nanoparticles are too large to pass through the semipermeable membrane and are therefore contained within the sensor. As the molecular target is not present, the nanoparticles are not aggregated.

Figure 2:
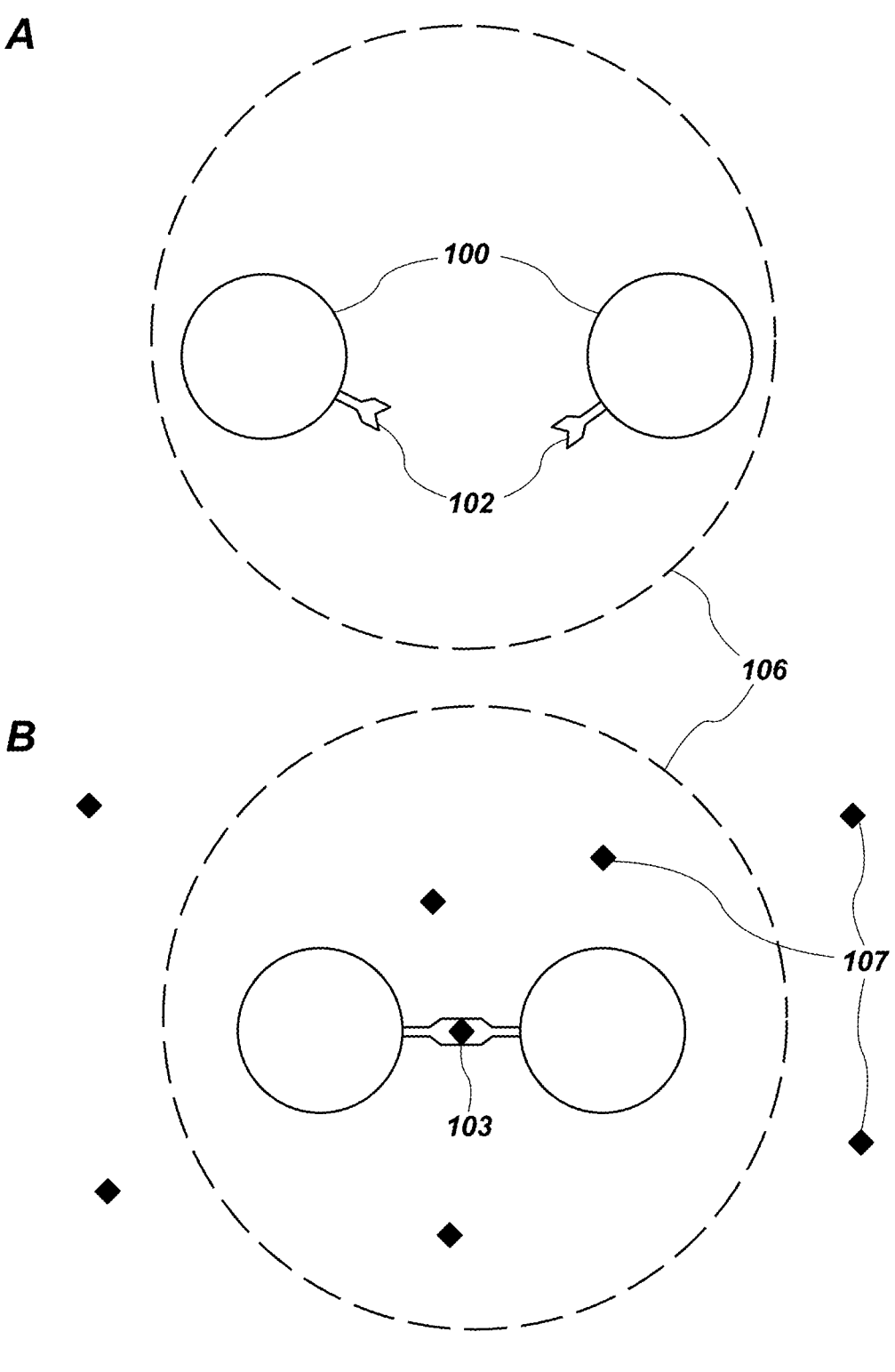
FIG. 2 illustrates functionalized nanoparticles in a semi-permeable container in unaggregated (A) and aggregated state (B).

In FIG. 2 B the biosensor is exposed to the free-floating targeted molecule 107. The targeted molecule is small enough to enter the sensor. The presence of the targeted molecule leads to a shared binding event 103 which aggregates the nanoparticles.

In another embodiment the biosensor consists of a non-magnetic matrix that contains nanoparticles. The matrix may be fully or partly biodegradable, the lifetime of the biosensor can be adjusted through the composition of the matrix. The matrix may consist of a biodegradeable material like Chitosan or Cellulose, Collagen, collagen vitrigel, Gelatin, Fibrin, Starch, Alginate, Polyhydroxyalkanoates (PHA), poly(glycolic acid) (PGA), PLA, PGLA, Poly(ε-caprolactone) (PCL), Polyanhydrides, Polyphosphazenes. The nanoparticles are unaggregated within the matrix or trapped within the matrix. The nanoparticles are functionalized to bind a targeted molecule. Upon exposure to the targeted molecule the nanoparticles aggregate with the targets and change their Neel relaxation time. The sensor can be designed as integrating, contemporary, or dispersing sensor or a combination thereof. This type of sensor will further be referred to as "matrix biosensor." The matrix biosensor can be produced in a variety of shapes, including a small-diameter pellets that can be injected with a small (18 gauge or smaller) syringe. Additionally, the disassembly of the container can be triggered by ultrasonication similar to Extracorporeal Shock Wave Lithotripsy for kidney stones.

FIG. 3A illustrates functionalized unaggregated nanoparticles within a biodegradable polymer matrix 108. The nanoparticles are unable to rotate freely but can still perform Neel relaxation. The structure of the polymer matrix is flexible enough so that the nanoparticles can reach each other. As the molecular target is not present the nanoparticles are not aggregated.

Figure 3:
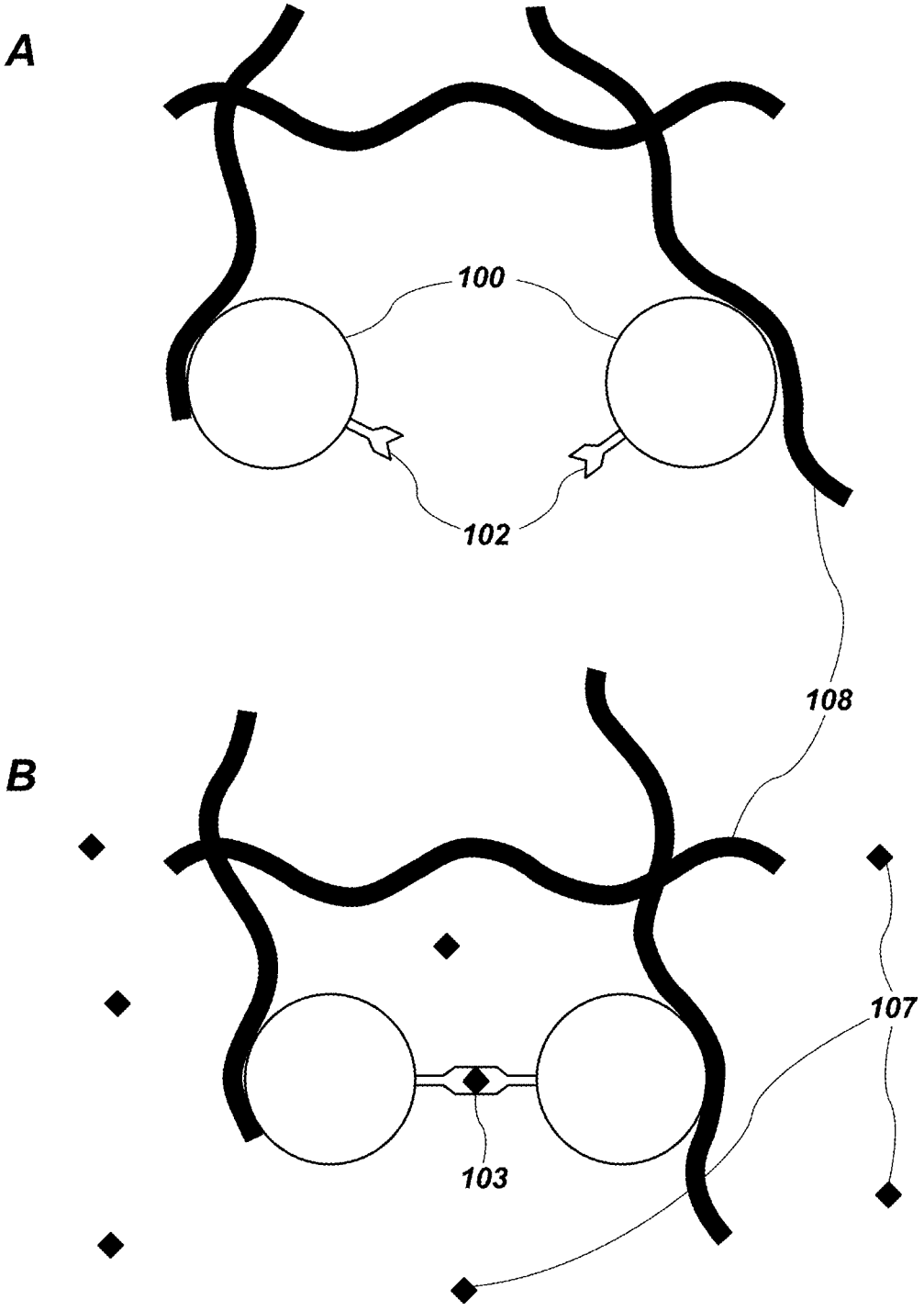
FIG. 3 illustrates functionalized nanoparticles in a matrix in unaggregated (A) and aggregated state (B).

In FIG. 3 B the biosensor is exposed to the free-floating targeted molecule 107. The targeted molecule is small enough to enter the polymer matrix and interact with the binding site of the functionalized nanoparticles. The presence of the targeted molecule leads to a shared binding event 103 which aggregates the nanoparticles.

In yet another implementation the biosensor contains functionalized nanoparticles and larger non-magnetic object such as nonmagnetic beads. The nanoparticles and non-magnetic objects are contained in a reservoir of the sensor. The nonmagnetic material may be biodegradable. One opening of the reservoir may have a semipermeable membrane. The functionalized nanoparticles are immobilized to the surface of the nonmagnetic material and are able to change their magnetic orientation through Neel relaxation. The nanoparticles are functionalized with binding sites to at least one molecular target. Upon exposure to the molecular target the nanoparticles cluster and change their Neel relaxation time. The sensor can be designed as integrating, contemporary, or dispersing sensor or a combination thereof.

FIG. 4A illustrates functionalized nanoparticles aggregated against a larger surface such as a nonmagnetic bead 110 or a nonmagnetic plate 109. The nanoparticles are unable to rotate freely but can still perform Neel relaxation. As the molecular target is not present the nanoparticles are not aggregated.

Figure 4:
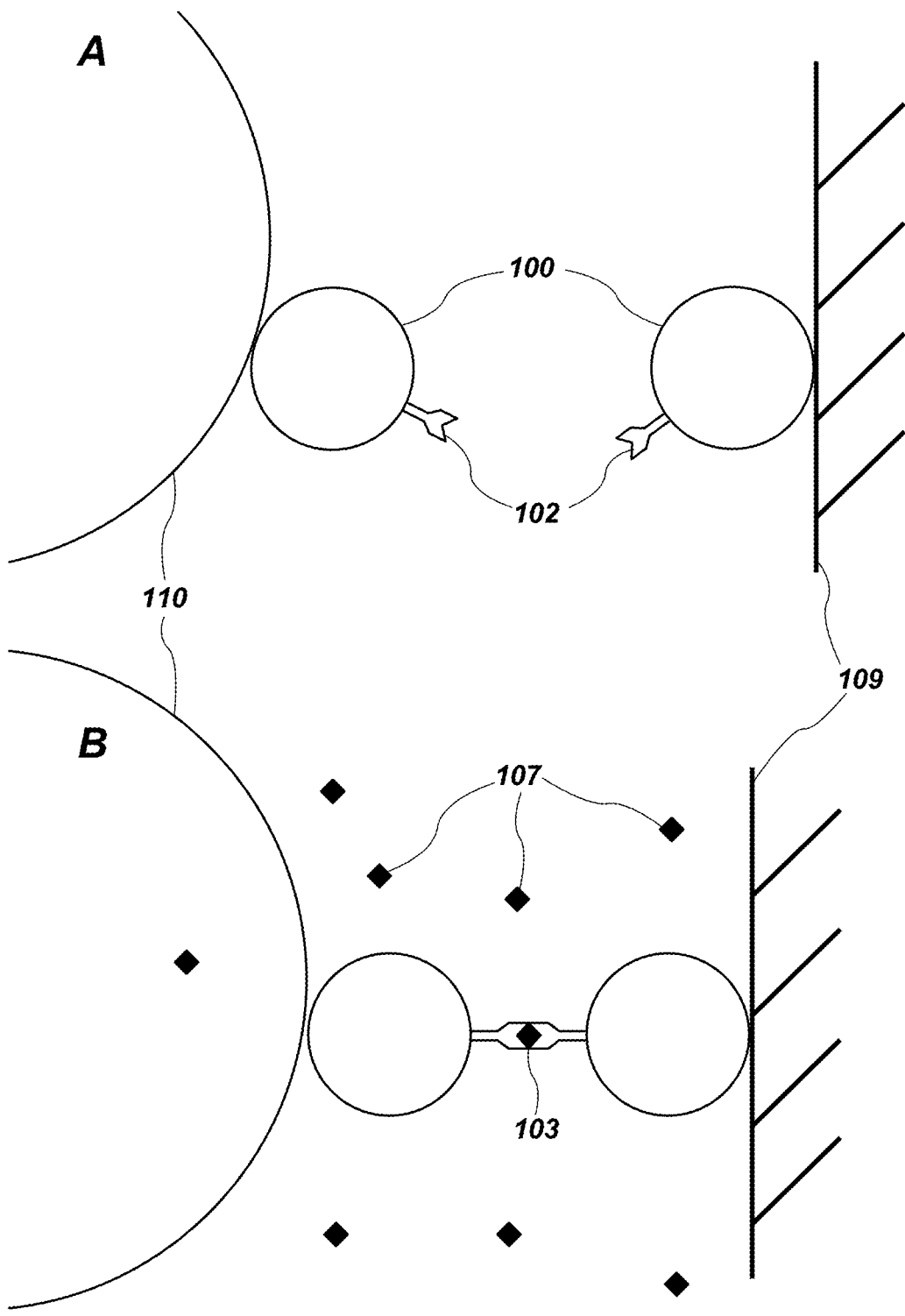
FIG. 4 illustrates functionalized nanoparticles combines with larger non-magnetic beads and surfaces in unaggregated (A) and aggregated state (B).

In FIG. 4 B the biosensor is exposed to the free-floating targeted molecule 107. The presence of the targeted molecule leads to a shared binding event 103 which aggregates the nanoparticles.

In yet another embodiment of the sensor the nanoparticles will be pre-aggregated with a molecule similar to the targeted molecule but weaker in binding affinity. If the targeted molecule is present it will compete with the pre-aggregation molecule for the same binding site in the nanoparticle. Due to the stronger affinity of the binding site to the targeted molecule it will replace the pre-aggregation molecule with the targeted molecule. Due to the surplus of weak and strong binding partners the nanoparticles are unlikely to share a single binding partner. The nanoparticle aggregation becomes less likely with higher concentrations of the targeted molecule in the draft area of the sensor, as the presence of the targeted molecule will break up the nanoparticle aggregates. The magnetic signal change of the sensor will therefore be the reverse of the integrating sensor. This type of sensor will further be referred to as "dispersing sensor." This type of sensor may have measurement advantages as it may respond faster to changes in the concentration of the target molecule. Additionally, this type of sensor may not need a semipermeable membrane, as the nanoparticle are initially contained in the pre-aggregated state.

FIG. 5A illustrates functionalized nanoparticles that have been pre-aggregated externally. The nanoparticles are aggregated through a binding molecule 111 that only has weak affinity to the nanoparticle's antibodies.

Figure 5:
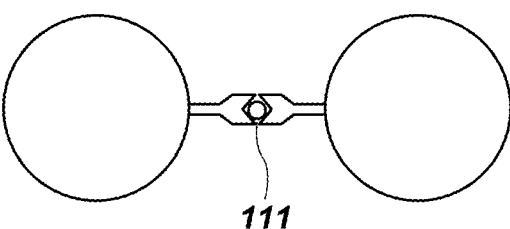
FIG. 5 illustrates functionalized nanoparticles pre-aggregated with a weak binding partner (A); after exposure to the strong binding targeted molecule the nanoparticles dissociate into an unaggregated state (B).
Figure 5:
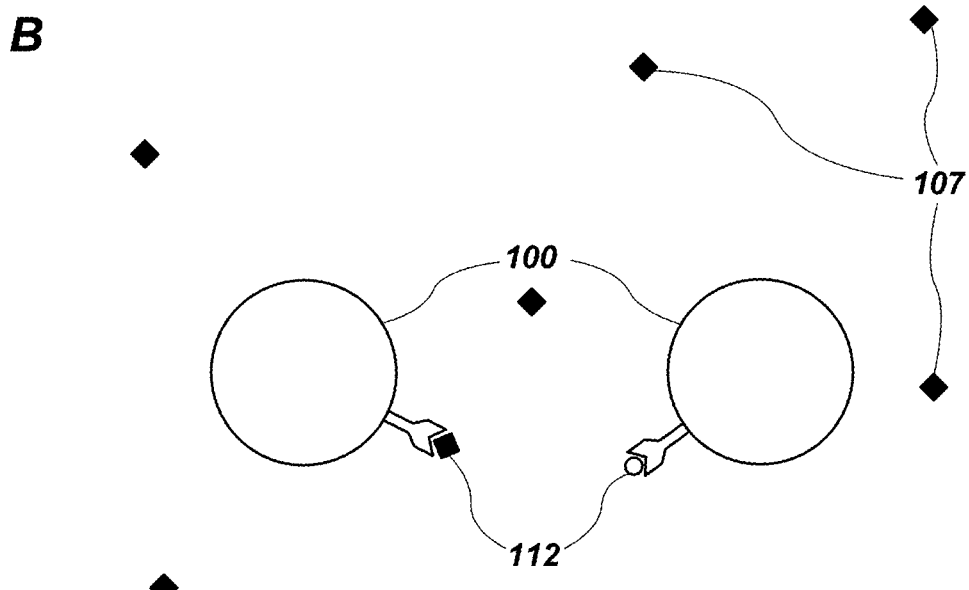

In FIG. 5 B the targeted molecule is present 107 and replaces the weak binding molecule as it has a stronger binding affinity. Due to the surplus of binding partners the aggregates dissolve 112.

In another implementation of the sensor the target of interest will be a molecular complex, consisting of a soluble drug bound to an endogenous molecule. For example, the nanoparticles within the sensor could have two types of functionalization. Type one binds to the injected drug, while type two binds only to the endogenous molecule. Only when the injected drug binds to the endogenous molecule the nanoparticles will aggregate. The change in magnetic signal would therefore be an indicator of the successful interaction of the drug with the target of interest at the implantation site. In an exemplary embodiment, the injected drug could be an Interleukin 2 (IL2) inhibitor which has an anti-IL2 binding site. The nanoparticles within the sensor have binding sites for the inhibitor drug as well as the endogenous IL2. Only when the injected drug binds to the endogenous IL2 can the nanoparticles aggregate and induce a change in the magnetic signal.

FIG. 6A illustrates functionalized nanoparticles in a non-aggregated state. The nanoparticles are functionalized with two different types of binding sites 115 & 116. Even in the presence of one binding partner, no aggregation occurs 115.

Figure 6:
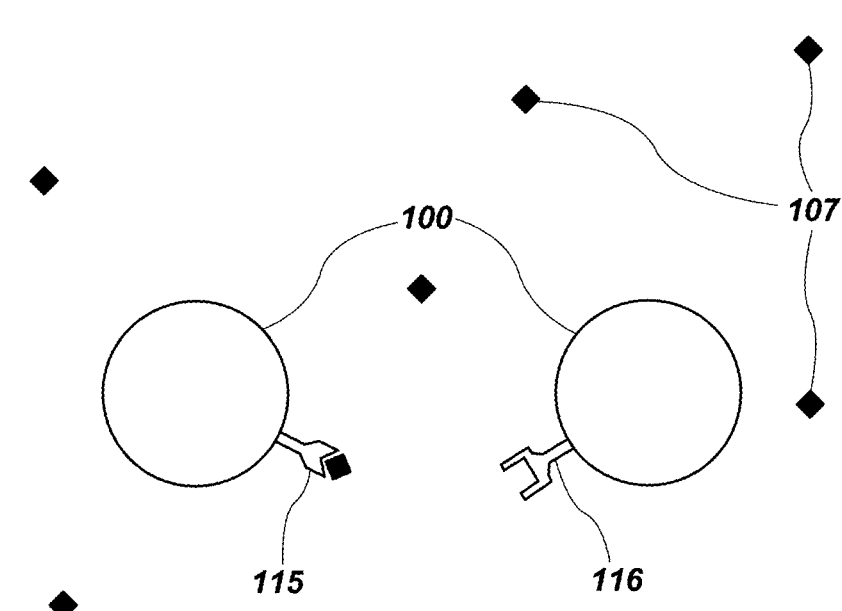
FIG. 6 illustrates functionalized nanoparticles in unaggregated (A) and aggregated state (B); upon exposure to a drug-molecule complex the nanoparticles and the complex aggregate.
Figure 6:
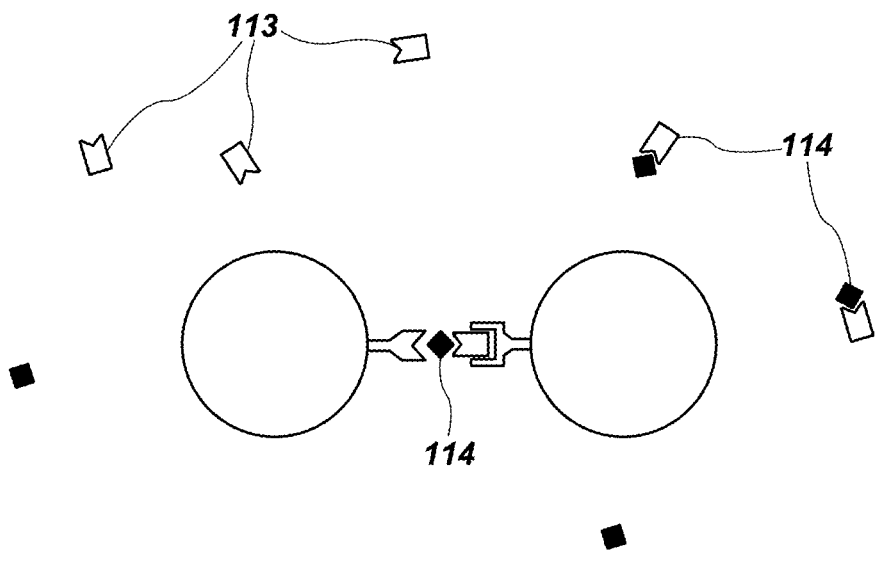

In FIG. 6 B the second targeted molecule is present 113 and interacts with the other, endogenous molecule 114. Due to the presence of both binding partners the nanoparticles now aggregate.

In an exemplary embodiment, the biosensor may be designed in a way that allows for minimally invasive implantation in the target site such as the tumor microenvironment. At the target site the sensor may further change its magnetic signaling response depending on the concentration of a targeted molecule in the draft area of the sensor. The change in magnetic signal response is due to changes in the Neel relaxation time and independent of changes in the viscosity of the extracellular media in the draft area. The change in the magnetic signaling response can be read out with AC spectroscopic means. For example, the nanoparticles within the implanted sensor aggregate due to exposure to the target of interest and alter their magnetic response signal due to dipolar interaction between the nanoparticles. The change is externally detected by a spectrometer which exposes the implanted sensor to an AC magnetic field and detects the magnetic response signal.

In another implementation, the biosensor is capable of detecting at least two different molecular targets. In this implementation the sensor contains at least two different types of nanoparticles that can be distinguished based on their magnetic signal. The nanoparticles may differ in core size, shape, anisotropy, material composition, coating, functionalization or a combination thereof. In one exemplary embodiment, one set of nanoparticles comprises a magnetic core with 20 nm diameter and a second set of nanoparticles comprises a core diameter of 25 nm. In the example the nanoparticles with 20 nm cores are functionalized with an antibody for tumor necrosis factor alpha (TNFa), while the nanoparticles with 25 nm cores are functionalized with antibodies for tumor necrosis factor beta (TNFb). In presence of TNFa only the 20 nm nanoparticles aggregate and change their signal whereas in presence of TNFb only the 25 nm nanoparticles aggregate.

In FIG. 7A two types of functionalized nanoparticles are illustrated. Where the first nanoparticle type 116 has a round shape and is functionalized for a specific molecular target, the second nanoparticle type 117 is cubical and functionalized for a different molecular target.

Figure 7:
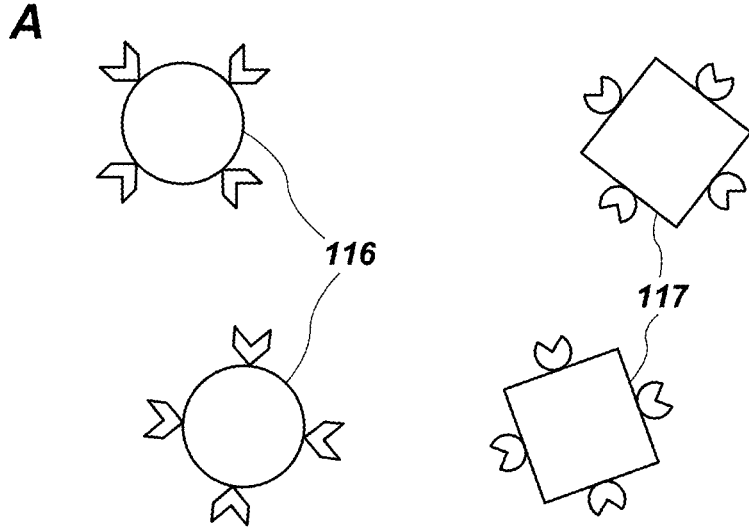
FIG. 7 illustrates two types of functionalized nanoparticles in unaggregated (A) and partially aggregated state (B); after exposure to the molecular target only one type of nanoparticle aggregates with the target; the other nanoparticle type is unaffected and stays unaggregated as it is functionalized for a different target.
Figure 7:
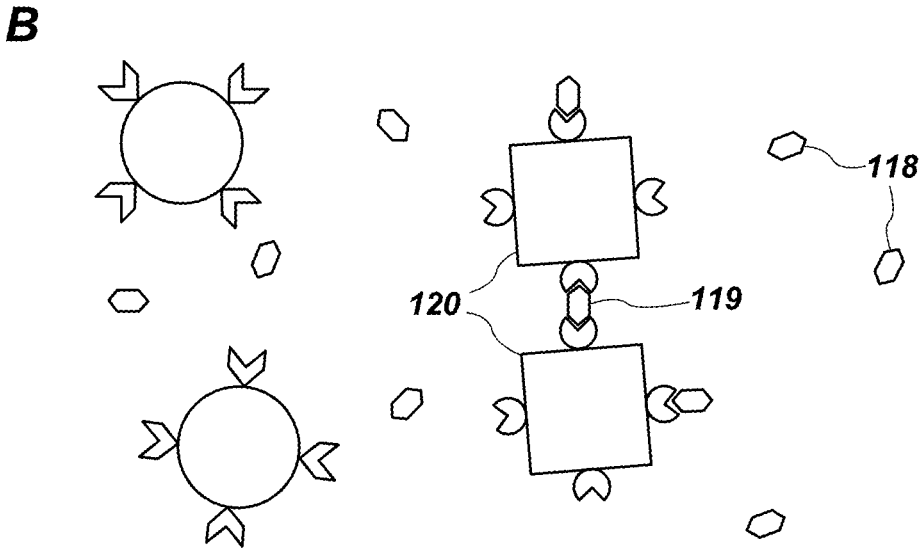

In FIG. 7 B one of the targeted molecules is present 118 and interacting with the nanoparticles. The cubical nanoparticles are functionalized for this specific target and binding to it 119. This causes the cubical nanoparticles to cluster 120. The change in magnetic signal can be used to determine the concentration of more than one molecular target.

In another exemplary embodiment, the molecular target of the sensor is a cytokine, a drug, RNA, DNA, a protein, a peptide, a sugar, a fat, a biosimilar, an antibody, an antibody fragment, or a combination thereof. The sensor may consist of a container with at least one semipermeable membrane which allows the targeted molecule to enter. Within the sensor may be nanoparticles that are functionalized with binding sites for the chosen molecular target. The biosensor may be implanted minimally invasive in the tumor microenvironment of a patient and configured to indicate the cumulative exposure of the sensor to the molecular target. The implanted sensor may further be analyzed by AC spectroscopic means.

Apparatus Description

An apparatus for detection of analytes in vivo, comprising functionalized magnetic nanoparticles, wherein each nanoparticle is combined with at least one binding moiety, wherein a relaxation time of the nanoparticles is dominated by Neel relaxation time at room temperature and at the chosen AC magnetic measurement frequency, wherein a non-magnetic coating and the charge on the nanoparticles enables dipole-dipole interaction between nanoparticle magnetic cores in aggregated form; an implantable, biocompatible container which retains the nanoparticles but allows analytes to enter and interact with the binding moieties on the nanoparticles; and a magnetization device which applies a magnetic field to magnetize nanoparticles within the biosensor in vivo and a measurement device which measures the Neel relaxation time of the nanoparticles by AC magnetic measurements.

The first part of the apparatus refers to several elements. The term "functionalized magnetic nanoparticles" in this context refers to particles that are at least in one dimension below 100 nm in size. Furthermore, the material the particles are made out of is paramagnetic, superparamagnetic, ferromagnetic, antiferromagnetic, ferrimagnetic, or diamagnetic. The particles comprise two components, a magnetic core, and a non-magnetic coating. The non-magnetic coating may further exhibit functional groups. Examples of these functional groups comprise amine groups, carboxyl-groups, sulfhydryl-groups, aldehyde-groups, hydroxyl-groups, azide-groups or a combination thereof. Examples of magnetic core materials comprise iron oxide, gadolinium-doped iron-oxide, yttrium-doped iron oxide, or copper-doped iron oxide. Furthermore, the shape of the nanoparticles may comprise spheres, rods, cubes, or discs, or a combination thereof.

The term "functionalization" in this context refers to the conjugation of molecules on the surface of the nanoparticles. Several methods of functionalization are known in the art. These methods include noncovalent binding such as adsorption or electrostatic interaction, or covalent binding such as coupling via NHS ester, hydrazide, maleimide or EDC coupling. Depending on the non-magnetic coating on the surface of the nanoparticles and the molecule that is to be conjugated to the surface, different functional groups are used. Examples of these functional groups are amine groups, carboxyl-groups, sulfhydryl-groups, aldehyde-groups, hydroxyl-groups, azide-groups or a combination thereof.

The term "binding moiety" in this context refers to a part of a molecule with capabilities to connect to other molecules. These bonds can be covalent or non-covalent, such as hydrogen bonds, electrostatic bonds, or Van der Waals forces. Examples of binding moieties are the binding sites on carbohydrates, peptides, pseudopeptides, peptoids, proteins, antibodies, antigens, aptamers, DNA, RNA, or molecularly imprinted polymers (MIP).

The Neel relaxation time is a property of magnetic materials defined as the mean time between two flips in magnetization of that material at a specific temperature. The Neel relaxation theory is known in the art.

The "measurement frequency" in this context refers to the frequency of the AC excitation magnetic signal. Examples of magnetic excitation signals are sine waves, triangular waves, sawtooth waves, ramp waves, square waves.

The "charge" of the particle in this context refers to the ion charge on the surface of the nanoparticle which can be positive, negative, or neutral. The colloidal stability of the nanoparticles and their ability to cluster in the presence of a target is influenced by the surface charge. Particle double layer theory is known in the art. Generally, charged particles in a solution are surrounded by ion with an opposing charge. In one example negative charged particles causes some of the positive ions to form a firmly attached layer around the surface of the particle; this layer of ion with opposing charge is known as the Stern layer. Around the Stern layer additional positive ions are still attracted but repelled by the firmly attached stern layer. These additional ions form the diffuse layer. The electrical potential at the junction between diffuse layer and stern layer is called the zeta potential and can be measured by various commercially available devices. The nanoparticles used in the apparatus are charged strong enough that they are stable in the interstitial fluid of the tumor microenvironment but can still interact to form aggregates in the presence of the target molecule; expressed as Zetapotential the charge would be between −30 mV and +30 mV.

One example of functionalized nanoparticles as described in part a) of the apparatus description are 20 nm iron oxide particles with carboxyl coating. In this example the particles are functionalized with biotin as binding moiety. Biotin forms a strong connection with streptavidin, which can bind up to 4 biotin molecules per molecule of streptavidin.

Figure 10:
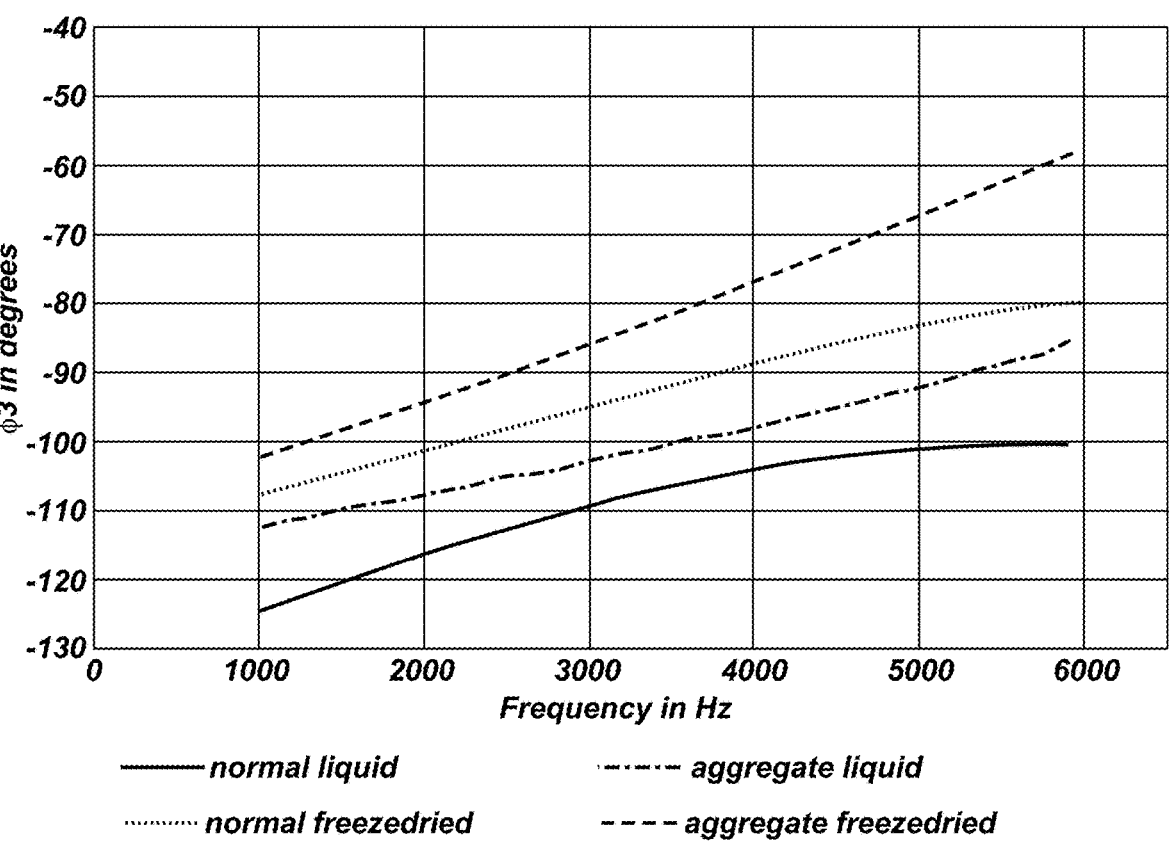
FIG. 10 shows the phase of the $3^{rd}$ harmonic, $\Phi3$, of 4 samples measured at different frequencies from 1000 Hz to 6000 Hz. The samples are each 10 ul of functionalized 20 nm iron oxide nanoparticles. All samples were functionalized with biotin, and some were aggregated by adding streptavidin. The solid black line shows the response of non-aggregated particles in water. The solid grey line shows the response of aggregated particles in water. The signal difference changes with the measurement frequency. The dotted black line shows the response of non-aggregated particles that have been immobilized via freeze drying with Mannitol. The dashed grey line shows the response of aggregated particles that have been immobilized via freeze drying with Mannitol. All measurements were carried out at room temperature. These measurements demonstrate that the signal contrast (phase difference between aggregated and normal particles) is independent of the mobility of the particles. Freeze dried and liquid particles have the same amount of signal change between aggregated and non-aggregated state, albeit at different frequencies. These results show that the signal contrast is caused by dipole-dipole interaction and not by interfering with the Brownian relaxation. All measurements have been carried out in vitro using the Nanoparticle Characterization Spectrometer—NCS (Lodestone Biomedical).

One streptavidin molecule can therefore connect at least two functionalized nanoparticles and cause aggregation. The aggregation for this functionalized nanoparticle caused significant dipole-dipole interaction, which can be demonstrated by analyzing the signal of liquid and immobilized (freeze dried) particles. FIG. 10 shows the phase of the $3^{rd}$ harmonic, $\Phi3$, of 4 samples measured at different frequencies from 1000 Hz to 6000 Hz. The samples are each 10 ul of functionalized 20 nm iron oxide nanoparticles. The solid black line shows the response of non-aggregated particles in water. The solid grey line shows the response of aggregated particles in water. The signal difference changes with the measurement frequency. The dotted black line shows the response of non-aggregated particles that have been immobilized via freeze drying with Mannitol. The dashed grey line shows the response of aggregated particles that have been immobilized via freeze drying with Mannitol. All measurements were carried out at room temperature. These measurements demonstrate that the signal contrast (phase difference between aggregated and normal particles) is independent of the mobility of the particles. Freeze dried and liquid particles have the same amount of signal change between aggregated and non-aggregated state, albeit at different frequencies. These results show that the signal contrast is caused by dipole-dipole interaction and not by interfering with the Brownian relaxation. All measurements have been carried out in vitro using the Nanoparticle Characterization Spectrometer—NCS (Lodestone Biomedical).

Further detailed descriptions of the biosensor and the nanoparticles can be found in the section "Biosensor Description." The term "implantable" in this context refers to the ability of the biosensor to be placed in parts or in its entirety within the body by a medical procedure and stay there after the procedure. One exemplary implantation technique is to place the sensor with the help of a needle, trocar, or stylet.

The term "biocompatible" in this context refers to the ability of a material to be in contact with the host organism without causing an adverse response. In the context of a biosensor this means in particular that the material does not cause an inflammation or foreign body response. Furthermore, the material should not interfere with the local concentration of the target molecule through adsorption or other mechanisms. Furthermore, the term biocompatible includes biodegradable materials. Examples of biodegradable materials are Chitosan or Cellulose, Collagen, collagen vitrigel, gelatin, fibrin, starch, alginate, polyhydroxyalkanoates (PHA), poly(glycolic acid) (PGA), PLA, PGLA, Poly(ε-caprolactone) (PCL), polyanhydrides, and polyphosphazenes.

The term "container" in this context refers to the ability of the biosensor component to retain the nanoparticles. This can be achieved in several ways. One way to retain the nanoparticles is to enclose them in a compartment or chamber. Another way to retain the nanoparticles is to link them to a larger structure such as a surface or matrix.

Figure 11:
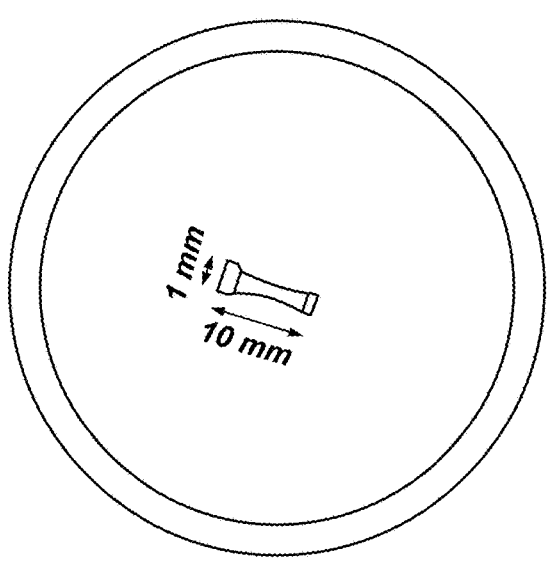
FIG. 11 shows an image of a nanoparticle filled biosensor in a small culture dish. The container in this example is a 500 kDa membrane out of polyvinylidene difluoride which has been heat sealed at the ends. Polyvinylidene difluoride demonstrated excellent biocompatibility. The container is roughly 1 mm in diameter and 10 mm in length. It contains approximately 5 ul of nanoparticle solution. The nanoparticles are 25 nm in diameter and too big to leave the 500 kDa membrane pores.

One example of a biocompatible container that retains nanoparticles is displayed in FIG. 11. The image shows a nanoparticle filled biosensor in a small culture dish. The container in this example is a 500 kDa membrane out of polyvinylidene difluoride which has been heat sealed at the ends. Polyvinylidene difluoride demonstrated excellent biocompatibility. The container is roughly 1 mm in diameter and 10 mm in length. It contains approximately 5 ul of nanoparticle solution. The nanoparticles are 25 nm in diameter and too big to leave the 500 kDa membrane pores.

The term "magnetization device" in this context refers to a component or assembly of component that generates a magnetic field powerful enough to influence the magnetic moment of the functionalized nanoparticles inside the biosensor. The magnetization device may comprise electromagnetic components, superconducting magnets, permanent magnets, or a combination thereof. In one example the magnetization device is an induction coil without ferromagnetic core. The coil creates a homogeneous magnetic field within its center when a current is applied. When an alternating current is applied the resulting magnetic field also exhibits alternating magnetic field directions. The coil has an inner diameter of at least 15 cm which allows small animals such as mice to move through the center of the coil. The host with implanted biosensor can then be moved through the center of the coil to be magnetized.

The term "measurement device" in this context refers to a component or assembly of component that detects the magnetic field. Several types of magnetic measurement devices are known in the art. These include but are not limited to direct current superconducting quantum interference devices, search coil, fluxgate, magnetoelectric, giant magneto-impedance, anisotropic/giant/tunneling magnetoresistance, optically pumped, cavity optomechanical, Hall effect, magnetoelastic, and spin wave interferometry. In one example the measurement device is a magnetoelectric coil configuration known in the art as gradiometer coil. The biosensor can be moved through the center of the coil configuration to be measured.

The term "AC magnetic measurements" in this context refers to the simultaneous magnetization and measurement of the biosensor using the before mentioned measurement device and magnetization device. In one implementation the measurement and magnetization device are parts of a larger machine. Simultaneous magnetization and detection may include analog or digital compensation of the magnetization signal. Several types of AC magnetic measurements are known in the art. The measurement may include the detection and recording of magnetization harmonics, hysteresis loops, remanence, coercivity, and/or maximal magnetization or a combination thereof.

Method Description

A method is disclosed for the detection of molecular targets comprising the following steps: a) providing biosensors with functionalized nanoparticles and minimally invasively implanting them in a subject; b) measuring the magnetic response of the implanted biosensors through one or several AC measurements; c) determining the positions of the implanted biosensors using algorithms, models and assumptions; d) positioning the AC detection unit in proximity to the implanted biosensor of interest and performing an AC measurement of the implanted biosensor of interest; e) isolating the functionalized nanoparticle signal of interest; and f) calculating the concentration of the analyte through from the magnetic response obtained in step e) and a calibration curve with known concentrations of the analyte.

Step a) of the method refers to the implantation of one or several biosensors using surgical techniques that are minimally-invasive. The term "minimally-invasive" in this context refers to entering the living body through a small incision or puncture. In an exemplary implementation the biosensor is implanted minimally-invasive using a biopsy needle and an ejector pin or a trocar.

Furthermore, the biosensor with functionalized nanoparticles can be provided by functionalizing functionalized nanoparticles and filling a biocompatible container with them which is then sealed. In one embodiment of the method the biocompatible container comprises at least one port with a semipermeable membrane. In an exemplary embodiment the biocompatible container is comprised of a cylinder made in its entirety out of a semipermeable membrane material such as polyvinylidene difluoride. The cylinder in this example is small enough to fit into a biopsy needle and can be heat-sealed on both ends after being filled with functionalized nanoparticles.

In another implementation the biosensor is comprised of a non-magnetic matrix that contains nanoparticles. The matrix may be fully or partly biodegradable, the lifetime of the biosensor can be adjusted through the composition of the matrix. The matrix may consist of a biodegradable material like chitosan or cellulose, collagen, collagen vitrigel, gelatin, fibrin, starch, alginate, polyhydroxyalkanoates (PHA), poly (glycolic acid) (PGA), PLA, PGLA, Poly(ε-caprolactone) (PCL), polyanhydrides, polyphosphazenes. The nanoparticles are aggregated within the matrix or trapped within the matrix. The form and shape of the matrix is small enough to fit into a biopsy needle, and, depending on the material, can be stiff, elastic or gel-like.

The term "functionalization" in this context refers to the conjugation of molecules on the surface of the nanoparticles. Several methods of functionalization are known in the art. These methods include noncovalent binding such as adsorption or electrostatic interaction, or covalent binding such as coupling via NHS ester, hydrazide, maleimide or EDC coupling. Depending on the non-magnetic coating on the surface of the nanoparticles and the molecule that is to be conjugated to the surface, different functional groups are used. Examples of these functional groups are amine groups, carboxyl-groups, sulfhydryl-groups, aldehyde-groups, hydroxyl-groups, azide-groups or a combination thereof.

In one exemplary demonstration the functionalization of nanoparticles with antibodies as target specific binding moieties has been carried out experimentally.

Functionalization of Carboxyl Iron Oxide Nanoparticles with Monoclonal Antibodies Using EDC Coupling In one example the functionalization of nanoparticles has been demonstrated using EDC (1-Ethyl-3-(3-dimethylaminopropyl) carbodiimide) coupling and carboxyl iron oxide nanoparticles.

Materials: The SHP25 nanoparticles were 25 nm in diameter and were provided by Ocean NanoTech (San Diego, CA, USA, catalog #: SHP25-02). The antibody used in the protocol was Bevacizumab, an FDA approved monoclonal antibody targeting Vascular Endothelial Growth Factor (VEGF). Bevacizumab was provided by selleckchem (Houston, TX, USA). Recombinant human VEGF was provided by PeproTech Inc. (Cranbury, NJ, USA). Other chemicals, including bovine serum albumin (BSA), phosphate buffered saline (PBS), Pierce™ EDC No-Weigh™ were provided by Thermo Fisher Scientific Inc. (Waltham, MA, USA). The MNP were mixed directly with the sample solution in phosphate buffered saline (PBS) to simulate the salt concentration in vivo. The activation and quenching buffers, as well as the magnetic separator were provided by Ocean NanoTech (catalog #: AB300-10, QB100-01, MMS-1.5).

Protocol

Remove EDC from the freezer. Let equilibrate to room temperature before opening. Dilute to desired concentration of 3 µg/µL with activation buffer $$\frac{1 \text{ mg}}{x \text{ mL}} = \frac{3 \text{ µg}}{1 \text{ µL}}, x = 0.333 \text{ mL}$$

or 333 uL of activation buffer
Dilute Bevacizumab to the desired concentration of 2 µg/µL with activation buffer $$\left(5\frac{g}{L}\right)*x = \left(2\frac{\text{µg}}{\text{µL}}\right)(100 \text{ µL}), x = 40 \text{ µL of } 5\frac{g}{1}BEV +$$

60 µL activation buffer
In a new tube, add 200 µL of the carboxyl nanoparticles (5 g/l) with 100 µL of activation buffer and 100 µL of the EDC solution. Incubate for 10 min at room temperature on nutator
Add 100 µL of the Bevacizumab solution. Incubate on nutator for 2 hours
Add 10 µL of quenching buffer and incubate for 10 min.
Separate the solution using magnetic separator, replacing 500 µL of PBS between each wash.
Experiment:
To simulate the aggregation behavior within the biosensor 10 ul of functionalized nanoparticles (concentration 0.7 g/l) each were mixed with various concentrations of VEGF solution. The total amounts of VEGF added were 150 ng, 300 ng, 500 ng, 650 ng and 800 ng, which compared to the number of nanoparticles can be expressed as molecule to MNP ratios of 9, 19, 31, 40 and 50, respectively. In a second series 10 ul of MNP (concentration 0.7 g/l) each were mixed with various concentrations BSA solution to check for nonspecific binding. The total amounts of BSA added were 175 ng, 613 ng, 805 ng, 963 ng and 1190 ng, which compared to the number of nanoparticles can be expressed as molecule to MNP ratios of 9, 31, 41, 49 and 61, respectively.

After mixing the particles with the target molecule solution each sample was toped of with PBS to a final volume of 15 ul and incubated at room temperature for 1 h. The samples were then measured in the nanoparticle characterization system (provided by Lodestone Biomedical) at 1000 Hz.

Figure 8:
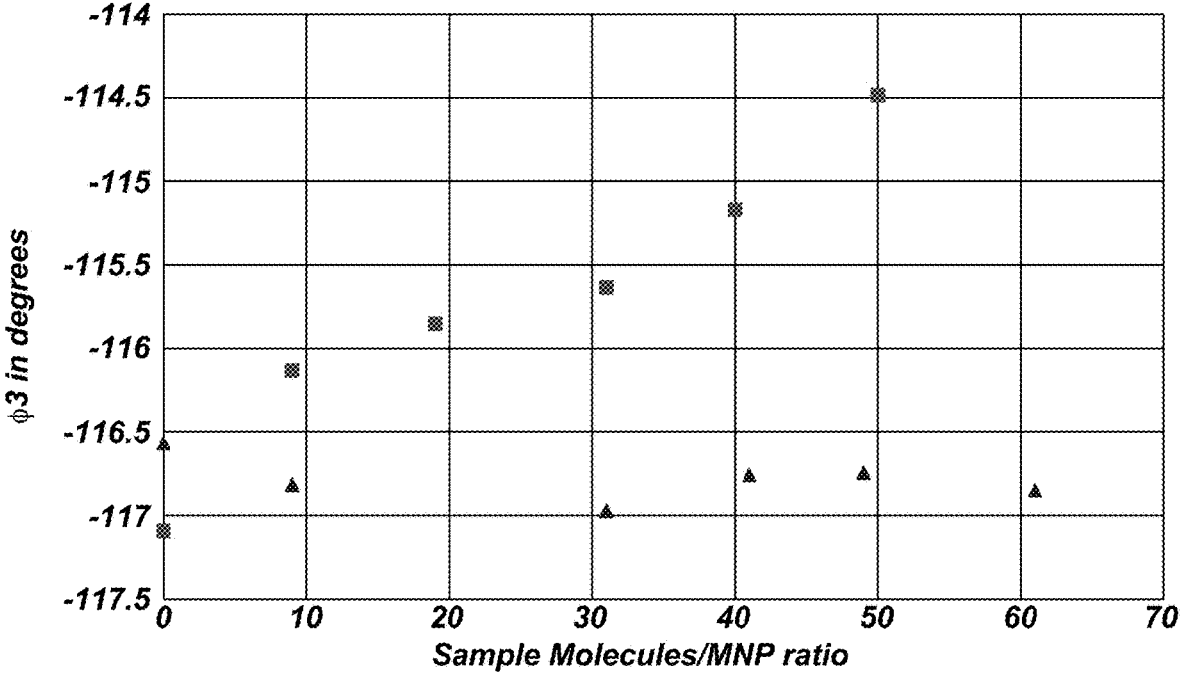
FIG. 8 shows the phase of the $3^{rd}$ harmonic, $\Phi3$, as the ratio of sample molecule to MNP increases. The MNPs have been functionalized to bind to the Vascular Endothelial Growth Factor (VEGF) molecule. Adding increasing amounts of VEGF changes $\Phi3$. Adding bovine serum albumin (BSA) on the other hand does not influence the phase. The MNP were mixed directly with the sample solution in phosphate buffered saline (PBS) to simulate the salt concentration in vivo. All measurements have been carried out in vitro using the Nanoparticle Characterization Spectrometer—NCS (Lodestone Biomedical).

The harmonic spectrum of the NCS measurements displays a linear relationship between VEGF concentration and the phase of the $3^{rd}$ harmonic, $\Phi_3$. Whereas no effect on the phase could be detected for increasing BSA concentrations. The phase of the $3^{rd}$ harmonic, $\Phi_3$, is displayed against the sample molecule/MNP ratio in FIG. 8. The overall change in phase between 0 ng of VEGF and 800 ng is 2.5 degrees. The experiment therefore successfully demonstrated the specific detection capabilities of the nanoparticle aggregation assay. Various Functionalization Options of Carboxyl Iron Oxide Nanoparticles with Monoclonal Antibodies Using EDC Coupling In another example various functionalization processes of functionalized nanoparticles have been demonstrated using EDC coupling and carboxyl iron oxide nanoparticles. The influence of the different factors on the phase change have been investigated.

The variable parameters were:

Particle size: 20 nm vs 25 nm

Coupling chemistry: sulfo NHS vs no sulfo NHS

Antibody size: Bevacizumab (150 kDa) vs Ranibizumab (50 kDa)

Quenching buffers: Ocean NanoTech QB, Glycine Buffer 0.2M, pH 7.4, 4-(2-aminoethyl) morpholine, 2-(2-methoxyethoxy) ethanamine, N,N dimethylethylenediamine, hydroxylamine HCl Materials: The SHP25 and SHP20 nanoparticles were 25 nm in diameter and were provided by Ocean NanoTech (San Diego, CA, USA, catalog #: SHP25-02, SHP20-02). The antibodies used in the protocol were Bevacizumab and Ranibizumab, both FDA approved monoclonal antibody targeting Vascular Endothelial Growth Factor (VEGF). Ranibizumab is an antibody fragment only a third of the size of a full IGG antibody. Bevacizumab and Ranibizumab were provided by selleckchem (Houston, TX, USA).

Recombinant human VEGF was provided by PeproTech Inc. (Cranbury, NJ, USA). Other chemicals, including bovine serum albumin (BSA), phosphate buffered saline (PBS), Pierce™ EDC No-Weigh™, BupH™ PBS Buffer, BupH™ MES Buffered Saline, Sulfo-NHS No-weigh format, N,N dimethylethylenediamine, hydroxylamine HCl, were provided by Thermo Fisher Scientific Inc. (Waltham, MA, USA). The MNP were mixed directly with the sample solution in phosphate buffered saline (PBS) to simulate the salt concentration in vivo. The quenching buffer, as well as the magnetic separator were provided by Ocean NanoTech (catalog #: QB100-01, MMS-1.5).

The other quenching buffers 4-(2-aminoethyl) morpholine, 2-(2-methoxyethoxy) ethanamine were provided by Sigma Aldrich (Burlington, MA, USA). The Glycine Buffer 0.2M, pH 7.4 was provided by bioworld (Dublin, OH, USA).

Protocol

Remove EDC from the freezer. Let equilibrate to room temperature before opening. Dilute to desired concentration of 3 µg/L with activation buffer (BupH MES)

$$\frac{1\ mg}{x\ mL} = \frac{3\ \mu g}{1\ \mu L}, x = 0.333\ mL\ or\ 333\ uL$$

of activation buffer

Reconstitute 2 mg of sulfo-NHS to 1.5 mg/mL by adding 1.3 mL of activation buffer (BupH MES)

Dilute Bevacizumab to the desired concentration of 2 µg/µL with activation buffer (BupH MES)

$$\left(5\frac{g}{L}\right) * x = \left(0.5\ \frac{\mu g}{\mu L}\right)(100\ \mu L), x = 10\ \mu L\ of\ 5\frac{g}{1}BEV\ +$$

90 µL activation buffer

In a new tube, add 200 µL of the carboxyl nanoparticles (5 g/l) with 100 µL of activation buffer (BupH MES) and 50 µL of the EDC solution and 50 µL of 1.5 mg/mL sulfo-NHS. Incubate for 10 min. at room temperature on nutator Add 400 µL of Coupling buffer (BupH™ PBS Buffer) and 100 µL of 0.5 g/L Bevacizumab. Incubate for 2 h at room temperature on nutator Separate the solution using magnetic separator, replacing 500 µL of PBS between each wash.

Experiment

To simulate the aggregation behavior within the biosensor 10 ul of functionalized nanoparticles (concentration 0.6-0.8 g/l) each were mixed with various concentrations of VEGF solution. The total amounts of VEGF added were 150 ng, 300 ng, 500 ng, 650 ng and 800 ng, which compared to the number of nanoparticles can be expressed as molecule to MNP ratios between 5 and 40 depending on the particle concentration. After mixing the particles with the target molecule solution each sample was toped of with PBS to a final volume of 15 ul and incubated at room temperature for 1 h. The samples were then measured in the nanoparticle characterization system (provided by Lodestone Biomedical) at 1000 Hz.

Results

Figure 9:
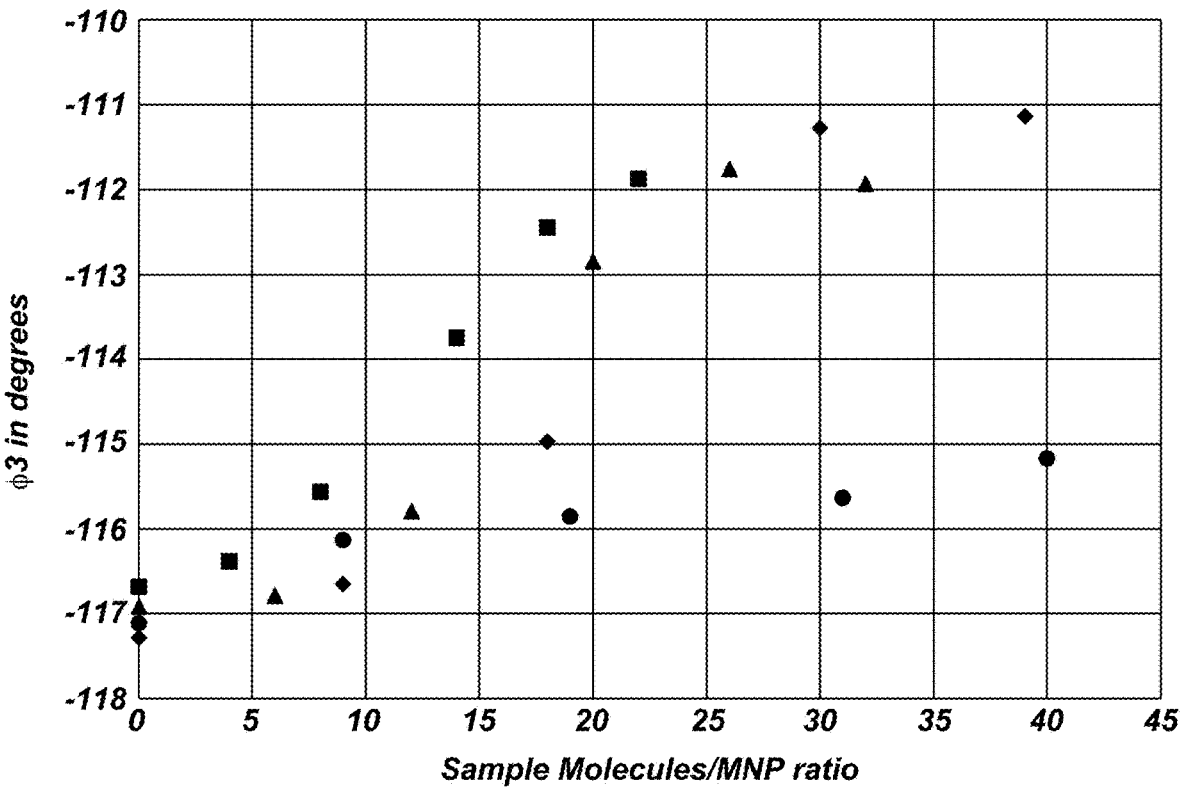
FIG. 9 shows the phase of the $3^{rd}$ harmonic, $\Phi3$, as the ratio of sample molecule to MNP increases. Four different functionalized nanoparticles are presented. They differ in particle size (20 nm vs 25 nm), crosslinking chemistry (sulfo NHS vs no sulfo NHS), and quenching buffer (Ocean Nanotech quenching buffer vs Glycene). All MNPs have been functionalized to bind to the Vascular Endothelial Growth Factor (VEGF) molecule using Bevacizumab. Adding increasing amounts of VEGF changes $\Phi3$. The MNP were mixed directly with the sample solution in phosphate buffered saline (PBS) to simulate the salt concentration in vivo. All measurements have been carried out in vitro using the Nanoparticle Characterization Spectrometer—NCS (Lodestone Biomedical).

Not all protocol variations were capable of producing stable nanoparticles. The quenching buffers 4-(2-aminoethyl) morpholine, 2-(2-methoxyethoxy) ethanamine, N,N dimethylethylenediamine, and hydroxylamine HCl did not result in usable particles. Protocols using the Ocean Nanotech quenching buffer or Glycine Buffer did result in stable particles. Of those protocols that worked some are displayed in FIG. 9. The harmonic spectrum of the NCS measurements displays a linear relationship between VEGF concentration and the phase of the $3^{rd}$ harmonic, $\Phi3$ for each series. The phase of the $3^{rd}$ harmonic, $\Phi3$, is displayed against the sample molecule/MNP ratio. The overall change in phase between 0 ng and 800 ng of VEGF is 2.5 degrees for the sample without sulfo-NHS. Selected samples that used sulfo-NHS in their coupling protocol and glycine or the Ocean NanoTech QB showed a larger signal change of 5 to 6 degrees. The nanoparticle size did not seem to affect the scale of the signal change at this frequency. Functionalization with Ranibizumab was successfully carried out and tested. However, the smaller antibody size did not affect the scale of the signal change. The experiment therefore successfully demonstrated the influence of the surface chemistry on the particle stability and signal change.

A biosensor can be equipped with more than one type of nanoparticles to enable multiplexing. The term "multiplexing" in this context refers to the quantification of more than one molecular target within one subject. In this implementation the biosensor contains at least two different types of nanoparticles that can be distinguished based on their magnetic signal. The nanoparticles may differ in core size, shape, anisotropy, material composition, coating, functionalization or a combination thereof. In one exemplary embodiment, one set of nanoparticles comprises a magnetic core with 20 nm diameter and a second set of nanoparticles comprises a core diameter of 25 nm. In the example the nanoparticles with 20 nm cores are functionalized with an antibody for tumor necrosis factor alpha (TNFa), while the nanoparticles with 25 nm cores are functionalized with antibodies for tumor necrosis factor beta (TNFb). In the presence of TNFa only the 20 nm nanoparticles aggregate and change their signal whereas in the presence of TNFb only the 25 nm nanoparticles aggregate.

In step b) of the method the subject with the implanted biosensor is exposed to AC magnetic fields partly or in its entirety. During the exposition, the magnetic field is also measured using state of the art magnetic detection components, such as coils, gradiometer coils, SQUID sensors, GMR sensors, or optical magnetometers. The measurement process may consist of a single or several point measurements and may include a linear scan. In case of the linear scan procedure the subject or the magnetic sensor is moved. The measurement process may also include the rotation of the magnetic sensor, the AC magnetic field generator or both. The magnetic field generated by the system may generate a magnetic gradient. In one embodiment the magnetic field gradient generated by the AC magnetic field generator varies in time. In another embodiment the magnetic field generated by the AC magnetic field generator varies in frequency. In yet another embodiment the magnetic field generated by the AC magnetic field generator varies in phase. In an embodiment the magnetic measurement comprises the harmonic spectrum obtained by Fourier transformation of the detected AC signal. In other implementations of the method the AC measurement obtains measurable parameters such as remanence, coercivity, maximal magnetization, or hysteresis loop parameters.

Figure 13:
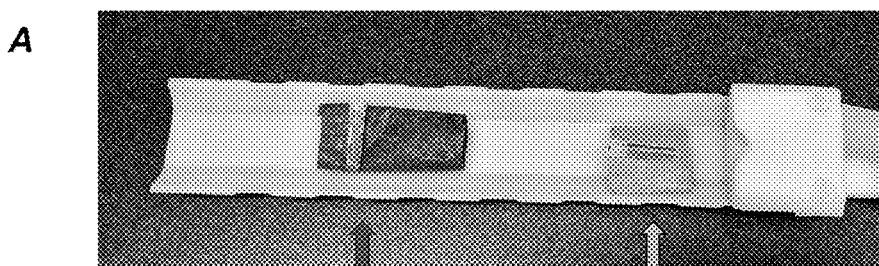
FIG. 13 shows a linear scan of two biosensors at the same time. The biosensors are placed in 50 ul capsules filled with water. The two biosensors are placed 7 cm apart on a sample stage (Frame A). The sample stage is then moved linearly through the magnetization and detection coils of the AC spectrometer. In frame B the amplitude of the third harmonic is displayed as a function of scan position. The position of the two probes along the linear axis can be identified on the peak positions of the $3^{rd}$ harmonic amplitude (indicated with arrows). All samples were measured at room temperature in vitro using the small animal spectrometer prototype (Lodestone Biomedical).
Figure 13:
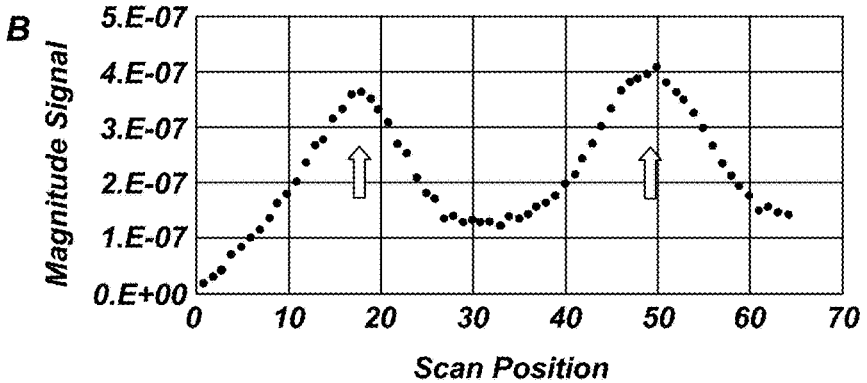

One example demonstration of a linear scan procedure with two biosensors is displayed in FIG. 13. The biosensors are placed in 50 ul capsules filled with water. The two biosensors are placed 7 cm apart on a sample stage (Frame A). The sample stage is then moved linearly through the magnetization and detection coils of the AC spectrometer. In frame B the amplitude of the third harmonic is displayed as a function of scan position. The position of the two probes along the linear axis can be identified on the peak positions of the $3^{rd}$ harmonic amplitude (indicated with arrows). Based on this linear scan detailed readouts can be performed at the identified peak positions.

In step c) of the method, the position of the implanted biosensors is determined based on the magnetic response measured in step b). The position of the implanted biosensors may be used to optimize the magnetic readout quality in subsequent measurements (step d) and to isolate the magnetic response of individual biosensors (step e). The magnetic readout quality is optimal when the magnetic detection component is closest to the implanted biosensor. One example of determining the position of the biosensor is to use a linear scan, moving the sensor or the subject through a heterogeneous magnetic field. The position of the biosensor can then be estimated based on the magnetic field strength measured along the scan axis. In another implementation of the method the position of the biosensors is calculated using algorithms, models and assumptions. One example in which the position of the biosensors is calculated uses a multiple magnetic dipole model with a known number of dipoles. In this example the Levenberg-Marquardt algorithm is used and the assumption is made that the biosensors behave like ideal dipoles.

Figure 12:
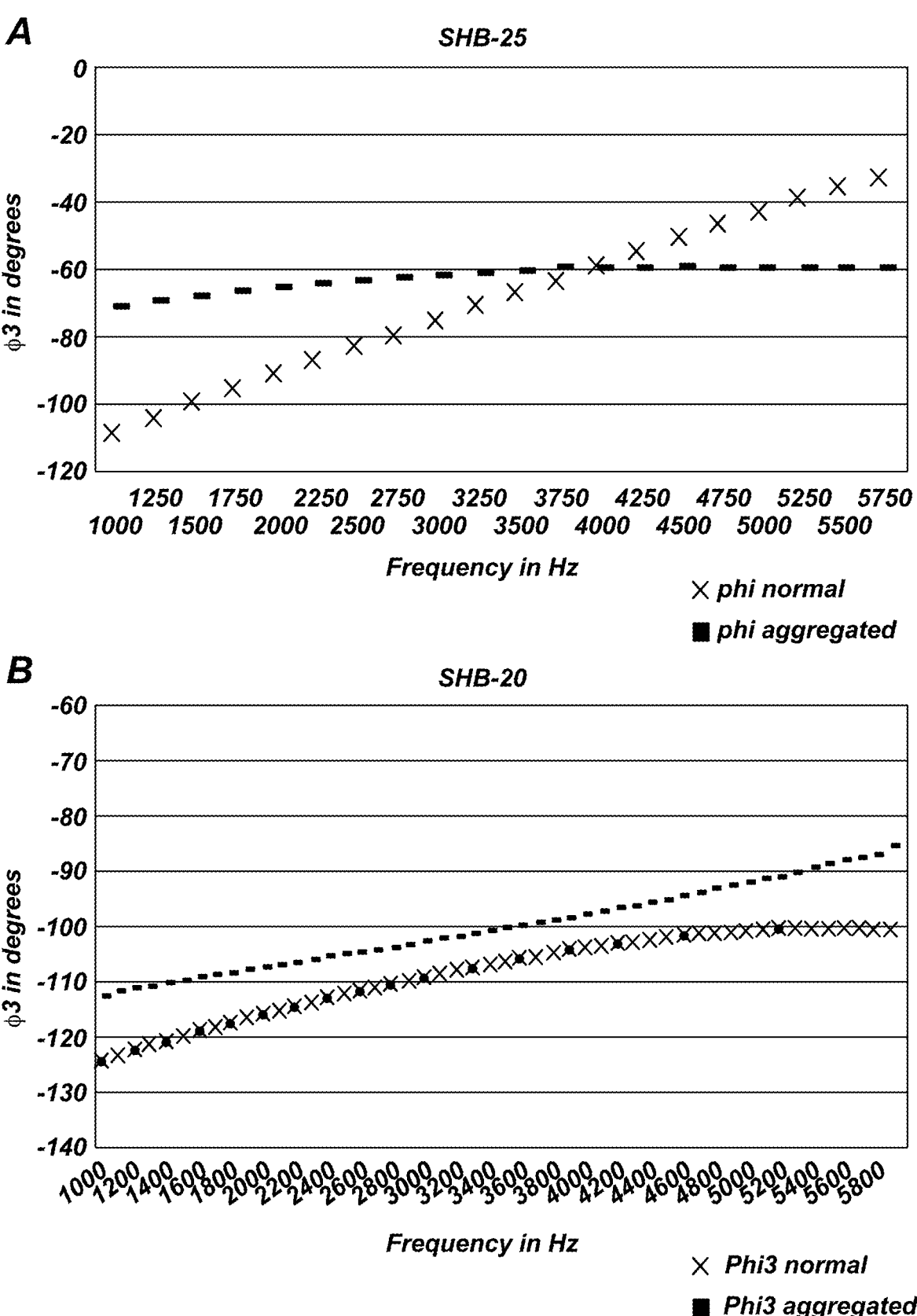
FIG. 12 shows the phase of the $3^{rd}$ harmonic, $\Phi3$, of 4 samples measured at different frequencies from 1000 Hz to 6000 Hz. The samples in frame A are each 10 ul of functionalized 25 nm iron oxide nanoparticles. The samples in frame B are each 10 ul of functionalized 20 nm iron oxide nanoparticles. All samples were functionalized with biotin, and some were aggregated by adding streptavidin. The frequency sweep reveals the frequency dependence of the signal contrast (phase difference between aggregated and normal particles). For the 25 nm particles the signal contrast is the most profound at 1000 Hz. At 3750 Hz the signal contrast of the 25 nm particles is not detectable. The 20 nm particles show a similar dependency but less pronounced. These frequency dependencies can be used for multiplexing, the measurement of several different particles at the same time. In one example the measurement at 3750 Hz would limit the influence of the 25 nm particles on the total signal and would allow the quantification of the 20 nm signal contrast. All samples were measured at room temperature in vitro using the Nanoparticle Characterization Spectrometer—NCS (Lodestone Biomedical).

In step e) of the method the magnetic signal of the nanoparticle type of interest is isolated by various means. In one implementation of the method the nanoparticles in the probe are exposed to a set of different frequencies. An example of frequency dependent signal is shown in FIG. 12.

In this example demonstration the phase of the $3^{rd}$ harmonic was measured from 20 nm and 25 nm particles at frequencies between 1000 Hz and 6000 Hz. The frequency sweep reveals the frequency dependence of the signal contrast (phase difference between aggregated and normal particles). For the 25 nm particles the signal contrast is the most profound at 1000 Hz. At 3750 Hz the signal contrast of the 25 nm particles is not detectable. These frequency dependencies can be used for multiplexing, the measurement of several different particles at the same time. In one example the measurement at 3750 Hz would limit the influence of the 25 nm particles on the total signal and would allow the quantification of the 20 nm signal contrast.

Because the different nanoparticle types create different nonlinear responses at different frequencies, the contribution of each nanoparticle type and their aggregation status can be calculated. The nanoparticles can be in the same biocompatible container or in different containers. In another implementation the different nanoparticle types can be differentiated based on their magnetic saturation. Depending on the type of nanoparticle the magnetic saturation is reached at different field strengths. After magnetic saturation is reached the magnetic response of the nanoparticle changes from non-linear to linear. The magnetic saturation can be reached through adding magnetic offset fields to the AC measurement. With the help of local offset fields other biosensor implants that are not of interest can be driven to saturation. To a limited extent this can be applied to nanoparticles in the same biocompatible container filled with different types of nanoparticles. In one implementation of the method the signal measurement and isolation of steps d) and e) comprises background subtraction to isolate the signal of interest from other background signals picked up by the detection system. In yet another implementation of the method steps d) and e) apply the use of surface coils that are placed above implanted biosensors. The surface coils can help decouple the signal from two biosensors through exposing them to different fields and frequencies.

In step f) of the method the isolated magnetic signal of the nanoparticles is compared to a known standard curve. In one implementation of the method the binding capabilities of the nanoparticles is permanent. In this case the sensor will slowly accumulate the molecular target over time. The readout of the biosensor will therefore reflect the total amount of target that the biosensor was exposed to since the beginning of the implantation. In another implementation of the method the binding capabilities of the nanoparticles are only temporary. In this implementation the magnetic signal change of the nanoparticles reflects the temporary concentration at the time of measurement.

In one exemplary application the method is used to indicate successful treatment with an immune system activating therapy, such as check-point blockade inhibitor therapy. In this example the biosensor is placed in the tumor microenvironment of a solid tumor. The nanoparticles in the biosensor are functionalized to detect a cytokine, a drug, RNA, DNA, a protein, a peptide, a sugar, a fat, a biosimilar, an antibody, an antibody fragmentor a combination thereof. Before treatment begin a baseline measurement of the molecular targets is performed, indicating the current concentration of the molecular targets in the vicinity of the biosensor. After treatment begins the biosensor is measured repeatedly over the course of several days. The accumulated concentration of the molecular targets is recorded during that time period. The clinician can use this information to judge whether T-cells in the tumor microenvironment have been successfully activated. Based on this information the patient and clinician can make an informed decision whether or not to continue the treatment, alter the treatment plan or change the treatment.

Figure 14:
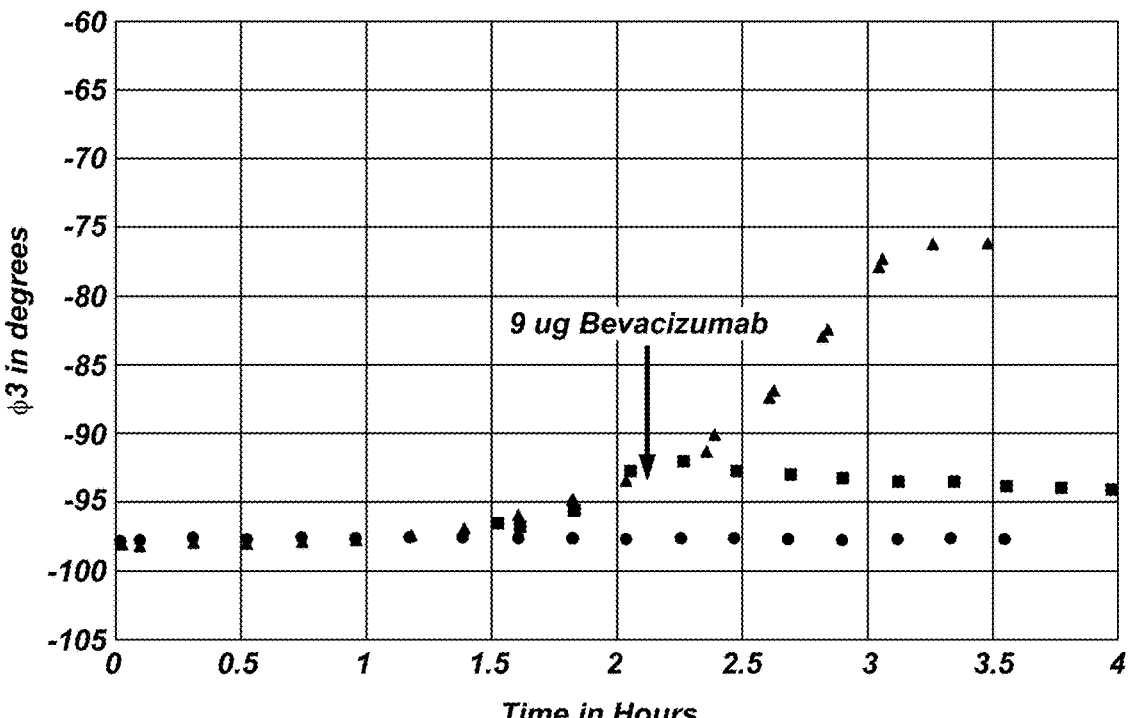
FIG. 14 shows the phase of the $3^{rd}$ harmonic, $\Phi3$, of 3 biosensors over the time of 4 hours. The 3 biosensors consist of 500 kDa membranes filled with functionalized 20 nm particles. The particles are functionalized to target VEGF. The grey circles represent the data of a biosensor that was not exposed to the target molecule. This biosensor did not display signal change in the measurement period. The black triangles represent the data of a biosensor that was exposed to 3 μg of VEGF at the beginning of the measurement period. The phase gradually changed as the target molecule diffused into the biosensor and the particles aggregated. The grey squares represent the data of a biosensor that was exposed to 3 μg of VEGF at the beginning of the measurement period but was additionally exposed to Bevacizumab (a VEGF inhibitor) after 2 h. Although the phase initially changed as the target molecules diffused into the biosensor, the signal change ceased when the VEGF molecules were blocked by Bevacizumab. These results demonstrate an exemplary use of the biosensor to measure cytokine activity in the tumor microenvironment (release of VEGF) and the detection of treatment response (VEGF blocking by Bevacizumab). All samples were measured at room temperature in vitro using the Nanoparticle Characterization Spectrometer—NCS (Lodestone Biomedical).

In one example the biosensor contains nanoparticles functionalized to detect Vascular endothelial growth factor (VEGF). VEGF is secreted by certain cancers to increase blood supply to the tumor. The monoclonal antibody treatment Bevacizumab can inhibit VEGF. The biosensor would in this example be placed in the tumor microenvironment and measure the local concentration of VEGF. Treatment with Bevacizumab would block the VEGF molecules around the tumor and limit blood vessel growth. An exemplary in vitro measurement with VEGF detecting biosensors is displayed in FIG. 14. The graph shows the phase of the $3^{rd}$ harmonic, Φ3, of 3 biosensors over the time of 4 hours. The 3 biosensors consist of 500 kDa membranes filled with functionalized 20 nm particles. The particles are functionalized to target VEGF. The grey circles represent the data of a biosensor that was not exposed to the target molecule. This biosensor did not display signal change in the measurement period. The black triangles represent the data of a biosensor that was exposed to 3 μg of VEGF at the beginning of the measurement period. The phase gradually changed as the target molecule diffused into the biosensor and the particles aggregated. The grey squares represent the data of a biosensor that was exposed to 3 μg of VEGF at the beginning of the measurement period but was additionally exposed to Bevacizumab (a VEGF inhibitor) after 2 h. Although the phase initially changed as the target molecules diffused into the biosensor, the signal change ceased when the VEGF molecules were blocked by Bevacizumab. These results demonstrate an exemplary use of the biosensor to measure cytokine activity in the tumor microenvironment (release of VEGF) and the detection of treatment response (VEGF blocking by Bevacizumab).

What is claimed is:

1. A system for detection of analytes, comprising:
a binding moiety;
functionalized nanoparticles combined with the binding moiety, each of the functionalized nanoparticles having:
    a nanoparticle magnetic core,
    a non-magnetic coating, and
    a charge,
    wherein the non-magnetic coating and the charge on the nanoparticles enables dipole-dipole interaction between nanoparticle magnetic cores of the functionalized nanoparticles in aggregated form;
an implantable, biocompatible container that retains the functionalized nanoparticles and is permeable to analytes that bind with the binding moieties on the functionalized nanoparticles; and a magnetization device configured to apply an alternating current (AC) magnetic field to the functionalized nanoparticles within the biosensor; and
a measurement device configured to:
    detect a magnetic response signal that includes AC magnetic measurements of the functionalized nanoparticles in the applied AC magnetic field,
    measure a Neel relaxation time of the functionalized nanoparticles based on the AC magnetic measurements of the magnetic response signal, and
    output the Neel relaxation time of the functionalized nanoparticles.

2. The system of claim 1, wherein the nanoparticles include one or more of iron oxide, gadolinium-doped iron-oxide, yttrium-doped iron oxide, or copper-doped iron oxide.

3. The system of claim 1, wherein the nanoparticles have a diameter between 1 and 100 nm.

4. The system of claim 1, wherein the non-magnetic coating includes a silica shell, a polymeric shell, a gold shell, a dextran shell, or a Polyethylene glycol (PEG) shell.

5. The system of claim 1, wherein a shape of the nanoparticles includes one or more of spheres, rods, cubes, or discs.

6. The system of claim 1, wherein the binding moiety includes one or more of a carbohydrate, a peptide, a pseudopeptide, a peptoid, a protein, an antibody, an antigen, an aptamer, DNA, RNA, or a molecularly imprinted polymer (MIP).

7. The system of claim 1, wherein the container further includes a sensor body having a reservoir, and wherein the nanoparticles are contained within the reservoir.

8. The system of claim 1, wherein the implantable, biocompatible container includes a semipermeable membrane that retains the functionalized nanoparticles in the container.

9. The system of claim 1, wherein the container includes a matrix having a polymer or polysaccharides retaining the nanoparticles in the aggregated form.

10. The system of claim 1, wherein the container also retains non-magnetic bodies, and wherein the functionalized nanoparticles are immobilized on a surface of the non-magnetic body.

11. The system of claim 1, wherein the container has a body with biodegradable material that includes one or more of Chitosan, Cellulose, Collagen, collagen vitrigel, gelatin, fibrin, starch, alginate, polyhydroxyalkanoates (PHA), poly (glycolic acid) (PGA), PLA, PGLA, Poly(ε-caprolactone) (PCL), polyanhydrides, or polyphosphazenes.

12. The system of claim 1, wherein the measurement device is further configured to measure a change in the Neel relaxation time of the functionalized nanoparticles based on the magnetic response signal by measuring a change in a total amount of targeted molecule to which the biosensor was exposed over time.

13. The system of claim 1, wherein the measurement device is further configured to measure a change in the magnetic signal related to a change in a concentration of a targeted molecule at the time of measurement.

14. The system of claim 1, wherein the functionalized nanoparticles are pre-aggregated in a pre-aggregated state with a weakly binding molecule that is replaced with a stronger binding targeted molecule when exposed, after which the functionalized nanoparticles change from the pre-aggregated state with a long Neel relaxation time to a not aggregated state with a short Neel relaxation time when exposed to the stronger binding targeted molecule.

15. The system of claim 1, wherein aggregation of the functionalized nanoparticles only occurs when at least two targeted molecules bind to each other and further bind to the functionalized nanoparticles.

16. The system of claim 1, wherein the biosensor is implanted minimally-invasively using a biopsy needle, during a tissue biopsy procedure.

17. The system of claim 1, wherein the biosensor is connected to a tether to create a biosensor-tether structure, and the biosensor-tether structure is partially implanted.

18. The system of claim 1, wherein the binding moiety is capable of selectively binding one or more of a cytokine, a drug, RNA, DNA, a protein, a peptide, a sugar, a fat, a biosimilar, an antibody, an antibody fragment, or a molecularly imprinted polymer (MIP).

19. The system of claim 1, wherein the biosensor is configured to indicate one or more of an accumulated concentration of a cytokine, a drug, RNA, DNA, a protein, a peptide, a sugar, a fat, a biosimilar, an antibody, an antibody fragment, or a molecularly imprinted polymer (MIP) after the biosensor is implanted.

20. The system of claim 1, wherein the functionalized nanoparticles have a charge between −30 mV and +30 mV.

21. The system of claim 1, wherein the AC magnetic measurements include detection and recording of magnetization harmonics, hysteresis loops, remanence, coercivity, or maximal magnetization.

22. The system of claim 1, wherein the functionalized nanoparticles are a first set of functionalized nanoparticles and further comprising a second set of functionalized nanoparticles having a different binding moiety than the first set of functionalized nanoparticles, wherein both the first set and the second set of functionalized nanoparticles are retained within the implantable, biocompatible container.

23. The system of claim 1, wherein the magnetization device is configured to apply the AC magnetic field at more than one frequency.

24. The system of claim 1, wherein the magnetization device is configured to apply the AC magnetic field to partially or entirely cause the functionalized nanoparticles into a magnetic saturation state.

25. The system of claim 1, wherein the measurement device is configured to determine a type of the functionalized nanoparticles based on a frequency-dependent magnetic response.

* * * * *